US007056684B2

(12) United States Patent
Madireddi

(10) Patent No.: US 7,056,684 B2
(45) Date of Patent: Jun. 6, 2006

(54) PROTEIN-PROTEIN INTERACTIONS OF P66$^{SHCA}$

(75) Inventor: Malavi Madireddi, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 152 days.

(21) Appl. No.: 10/658,995

(22) Filed: Sep. 10, 2003

(65) Prior Publication Data

US 2004/0115733 A1     Jun. 17, 2004

Related U.S. Application Data

(60) Provisional application No. 60/410,668, filed on Sep. 13, 2002.

(51) Int. Cl.
  G01N 33/53   (2006.01)
  C07K 14/00   (2006.01)
(52) U.S. Cl. .................................... 435/7.1; 530/350
(58) Field of Classification Search ................ 530/350; 435/7.1
  See application file for complete search history.

(56) References Cited

OTHER PUBLICATIONS

Sutovsky, P. et al, "Ubiquitinated Sperm Mitochondria, Selective Proteolysis, and the Regulation of Mitochondrial Inheritance in Mammalian Embryos", Biology of Reproduction, vol. 63, pp. 582-590 (2000).
Coates, P.J. et al, "Mammalian Prohibitin Proteins Respond to Mitochondrial Stress and Decrease during Cellular Senescence", Experimental Cell Research, vol. 265, pp. 262-273 (2001).
Sehnke, P.C. et al, "Interaction of a Plant 14-3-3 Protein with the Signal Peptide of a Thylakoid-Targeted Chloroplast Precursor Protein and the Presence of 14-3-3 Isoforms in the Chloroplast Stroma", Plant Physiology, vol. 122, pp. 235-241 (2000).
Jackson, J. et al, "Elevated Levels of p66 Shc Are Found in Breast Cancer Cell Lines and Primary Tumors with High Metastatic Potential", Clin. Cancer Res., vol. 6, pp. 1135-1139 (2000).
El-Shemerly, M. et al. "12-O-Tetradecanoylphorbol-13-acetate Activates the Ras/Extracellular Signal-regulated Kinase (ERK) Signaling Pathway Upstream of SOS Involving Serince Phosphorylation of Shc in NIH3T3 Cells", J. of Biological Chem., pp. 30599-30602 (1997).
Bonfini, L. et al, "Not all Shc's roads lead to Ras", TIBS, vol. 21, pp. 257-261 (1996).
Migliaccio, E. et al, "The p66shc adaptor protein controls oxidative stress response and life span in mammals", Nature, vol. 402, pp. 309-313 (1999).

Migliaccio, E. et al, "Opposite effects of the p52$^{shc}$/p46$^{shc}$ and p66$^{shc}$ splicing isoforms on the EGF receptor-MAP kinase-fos signalling pathway", EMBO J., vol. 16, No. 4, pp. 706-716 (1997).
Downward, Julian, "The GRB2/SEM-5 adaptor protein", FEBS Letters, vol. 338, pp. 113-117 (1994).
Kao, A. et al, "Insulin Stimulates the Phosphorylation of the 66- and 52-Kilodalton Shc Isoforms by Distinct Pathways", Endocrinology, vol. 138, No. 6, pp. 2474-2480 (1997).
Foschi, M. et al, "Endothelin-1 Induces Serine Phosphorylation of the Adaptor Protein p66$^{Shc}$ and Its Association with 14-3-3 Protein in Glomerular Mesangial Cells", J. of Biol. Chemistry, vol. 276, No. 28, pp. 26640-26647 (2001).
Yang, C. et al, "Taxol Mediates Serin e Phosphorylation of the 66-kDa Shc Isoform" Cancer Res., vol. 60, pp. 5171-5178 (2000).
Tavernarakis, N. et al, The SPFH domain: implicated in regulating targeted protein turnover in stomatins and other membrane-associated proteins, TIBS, pp. 425-427 (1999).
Langer, T. et al, "AAA proteases of mitochondria: quality control of membrane proteins and regulatory functions during mitochondrial biogenesis", Biochem. Soc. Trans., vol. 29, part 4, pp. 431-436 (2001).
Wang, S. et al, "Rb and Prohibitin Target Distinct Regions of E2F1 for Repression and Respond to Different Upstream Signals", Molecular Cell. Biol., vol. 19, No. 11, pp. 7447-7460 (1999).
Coates, P. et al, Mammalian Prohibitin Proteins Respond to Mitochondrial Stress and Decrease during Cellular Senescence, Experimental Cell Res., vol. 265, pp. 262-273 (2001).
Nijtmans, L. et al, "The mitochondrial PHB complex:roles in mitochondrial respiratory complex assemby, ageing and degenerative disease", CMLS, Cell Mol. Life Sci., vol. 59, pp. 143-155 (2002).
Nijtmans, L. et al, "Prohibitins act as a membrane-bound chaperone for the stabilization of mitochondrial proteins", EMBO J., vol. 19, No. 11, pp. 2444-2451 (2000).
Lotti, L. et al, "Shc Proteins Are Localized on Endoplasmic Reticulum Membranes and Are Redistributed after Tyrosine Kinase Receptor Activation", Molec. and Cell. Biol., vol. 16, No. 5, pp. 1946-1954.

(Continued)

*Primary Examiner*—Karen Cochrane Carlson
(74) *Attorney, Agent, or Firm*—John A. Lamerdin; Rosemarie R. Wilk-Orescan

(57) ABSTRACT

The present invention relates to (a) the establishment of a direct consequence to the mitochondrial import of phosphorylated p66$^{ShcA}$ and its association with prohibitin, and (b) to a potential function for the prohibitin-p66$^{ShcA}$ complex in the mitochondrial membrane depolarization process that governs metabolic events such as bioenergetics and free radical formation. The present invention can also be employed as a tool for identifying pharmaceutically active compounds that disrupt the prohibitin-p66$^{ShcA}$ interaction, thereby providing treatment options for aging-related diseases such as diabetes, cardiovascular, osteoporosis, cancer and neurodegenerative diseases.

13 Claims, 9 Drawing Sheets

OTHER PUBLICATIONS

Bunney, T. et al, "14-3-3 protein is a regulator of the mitochondrial and chloroplast ATP synthase", PNAS, vol. 98, No. 7, pp. 4249-5254.

Le, S. et al, "c-Jun N-terminal Kinase Specifically Phoshorylates p66$^{ShcA}$ at Serine 36 in Response to Ultraviolet Irradiation", J. of Biol. Chem., vol. 276, No. 51, pp. 48332-48336, (2001).

Nemoto, S. et al, Redox Regulation of Forkhead Proteins Through a p66shc-Dependent Signaling Pathway, Science, vol. 295, pp. 2450-2452 (2002).

McClung, J. et al, "Prohibitin:Potential Role in Senescence, Development, and Tumor Suppression", Exp. Gerontology, vol. 30, No. 2, pp. 99-124 (1995).

Oksvold, M. et al, "Immunocytochemical Localization of Shc and Activated EGF Receptor in Early Endosomes After EGF Stimulation of HeLa Cells", J. of Histochem CytoChem, vol. 48(1), pp. 21-33 (2000).

PROTEIN-PROTEIN INTERACTIONS OF P66$^{SHCA}$

The present patent application claims the benefit of U.S. Provisional Patent Application Ser. No. 60/410,668, filed Sep. 13, 2002, the disclosure of which is incorporated herein by reference in its entirety.

FIELD OF THE INVENTION

The present invention relates to novel protein-protein interactions involved in mammalian physiological pathways, including physiological disorders or diseases. Through the use of these novel protein-protein interactions, the present invention also relates to new targets for the identification of useful pharmaceuticals, new targets for diagnostic tools useful for the identification of individuals at risk of physiological disorders or diseases, and novel methods for therapeutic intervention in at least the physiological pathways described.

BACKGROUND OF THE INVENTION

Recent advances in human genomics research have led to rapid progress in the identification of novel and/or previously unidentified genes. In applications to biological and pharmaceutical research, there is a further need to determine the function of such identified gene products. A first step in defining the function of a novel gene is to determine its interactions with other gene products in an appropriate context. Since proteins make specific interactions with other proteins or biopolymers as part of functional assemblies or physiological pathways, a representative way to examine the function of a gene is to determine its physical relationship to one or more other genes.

Aging is a complex physiological phenomenon and the link between genes that regulate longevity and stress response is of great interest in the field of aging-related disorders such as diabetes, cancer, osteoporosis, cardiovascular and neurodegenerative diseases. The "free radical" theory of aging (Harman, (2001) *Ann. N.Y. Acad. Sci.* 928:1–21), and the central role that mitochondria play in this process, is gaining recognition. Proof of principle has been established in model systems such as *C. elegans*, *Drosophila* and recently in mouse (Guarente & Kenyon, (2000) *Nature* 408:255–62; Hayflick, (2000) *Nature* 408: 267–9; Lithgow & Andersen, (2000) *Bioessays* 22:410–3). Certain signaling pathways involved in the regulation of cell growth also participate in cellular response to oxidative stress (Zachary & Gliki, (2001) *Cardiovasc. Res.* 49:568–81). Growth factor receptors such as EGFR and PDGFR are activated on exposure to hydrogen peroxide ($H_2O_2$) (Kamata et al., (2000) *Eur. J. Biochem.* 267:1933–44). Activation of these receptors results in the recruitment and assembly of multi-protein signaling complexes at the membrane that ultimately result in gene expression changes that determine cellular fate (for a review, see, e.g., Liebmann, (2001) *Cell Signal* 13:777–85). One of the key mitogenic adapter proteins involved in this pathway is the Src Homologous Collagen-homologous protein, Shc family adapter protein (Ravichandran (2001) *Oncogene* 20:6322–30). The ShcA locus is highly conserved throughout evolution and encodes three overlapping proteins of 66, 52 and 46 kDa (Luzi et al., (2000) *Curr. Opin. Genet. Dev.* 10:668–74). Molecular and biochemical evidence suggests a role for p52/p46$^{ShcA}$ in receptor tyrosine kinase (RTK)-mediated signal transduction and activation of the Ras/MAPK pathway.

The most recently defined member of the family, p66$^{ShcA}$ is an anomaly in the mitogenic activity of ShcA (Bonfini et al., (1996) *Trends. Biochem. Sci.* 21:257–61). It differs from the other two ShcA proteins (p52/p46$^{ShcA}$) in that it has a second proline/glycine-rich domain (CH2) at the amino-terminus, which appears to confer different properties to this ShcA family member. Evidence suggests a role for it in stress pathways activated by insults such as UV irradiation and oxidation (Migliaccio et al., (1999) *Nature* 402:309–13).

Despite these advances, there continues to be a need in the art to identify protein-protein interactions that are involved in mammalian physiological disorders and diseases, and to thereby identify therapeutic targets for drug discovery.

The publications and other materials referenced herein by author to illuminate the background of the invention or to provide additional details regarding the practice of the invention, are incorporated by reference in their entirety.

SUMMARY OF THE INVENTION

In one aspect, the present invention relates to the discovery of novel protein-protein interactions that are involved in mammalian physiological pathways, including pathways implicated in physiological disorders and diseases, and to various uses of this discovery. The nucleotide sequences encoding the proteins of the present invention might have been known, but until the present disclosure, the potential interaction of these sequences in a physiological pathway or with a particular protein was unknown.

In another aspect of the present invention an isolated protein complex comprising a p66$^{ShcA}$ protein and a prohibitin protein is disclosed. In one embodiment, the protein complex comprises a p66$^{ShcA}$ sequence encoded by a polynucleotide comprising SEQ ID NO:1 and a prohibitin sequence encoded by a polynucleotide comprising SEQ ID NO:2. In other embodiments, the protein comprises a p66$^{ShcA}$ fragment and a prohibitin encoded by a polynucleotide comprising SEQ ID NO:2 or a p66$^{ShcA}$ encoded by a polynucleotide comprising SEQ ID NO:1 and a prohibitin fragment. In yet further embodiments, the protein complex comprises a p66$^{ShcA}$ protein encoded by a polynucleotide comprising a fragment of SEQ ID NO:1 and a prohibitin protein encoded by a polynucleotide comprising a fragment of SEQ ID NO:2. The present invention also encompasses the detection of the aforementioned protein complexes that form the basis of the protein interactions.

In another aspect of the present invention, an isolated antibody that is selectively immunoreactive with a protein complex described herein is disclosed. Such an antibody can be a monoclonal antibody. An antibody of the present invention can be monoclonal or polyclonal, and while being immunoreactive with the protein complex, the antibody is not immunoreactive with the individual parts of the protein complex. That is, an antibody of the present invention is not immunoreactive with a first interacting protein alone, a fragment of a first interacting protein alone, a second interacting protein alone, or a fragment of a second interacting protein alone. Antibodies as described herein are useful for detecting the presence or absence of the protein complexes.

The present invention also relates to a method of identifying a compound capable of modulating the formation of a p66$^{ShcA}$-prohibitin protein complex. In one embodiment the method comprises the steps of: (a) combining a p66$^{ShcA}$ protein and a prohibitin protein in the presence of a test compound to form a first complex; (b) combining a p66$^{ShcA}$ protein and a prohibitin protein in the absence of the test compound to form a second complex; (c) measuring the amount of the first complex and said second complex; and (d) comparing the amount of the first complex with the amount of the second complex, wherein if the amount of the first complex is greater than, or less than the amount of the second complex, then the test compound modulates the formation of the protein complex.

Additionally, the present invention relates to a method of screening for a compound that can be employed in the treatment of a physiological disorder comprising the steps of: (a) measuring the activity of a protein selected from the proteins set forth in Table 1 in the presence of a test compound; (b) measuring the activity of the protein in the absence of the test compound; and (c) comparing the activity measured in steps (a) and (b), wherein a difference in activity indicates the test compound is a compound that can be employed in treatment of a physiological disorder.

In any embodiment of the present invention, a $p66^{ShcA}$ protein or fragment can comprise a mutation, such as S36A (encoded by SEQ ID NO:7) or S36D (encoded by SEQ ID NO:8).

Another aspect of the present invention comprises nucleic acids that encode novel proteins discovered in accordance with the present invention, as well as the corresponding proteins and antibodies.

Thus, it is an object of the present invention to provide protein-protein interactions that are involved in mammalian physiological disorders and diseases, as well as methods to identify therapeutic targets for drug discovery. The present invention solves these and other problems.

Some of the objects of the invention having been stated hereinabove, other objects will become evident as the description proceeds when taken in connection with the accompanying drawings as best described hereinbelow.

DETAILED DESCRIPTION OF THE INVENTION

Figure 1:
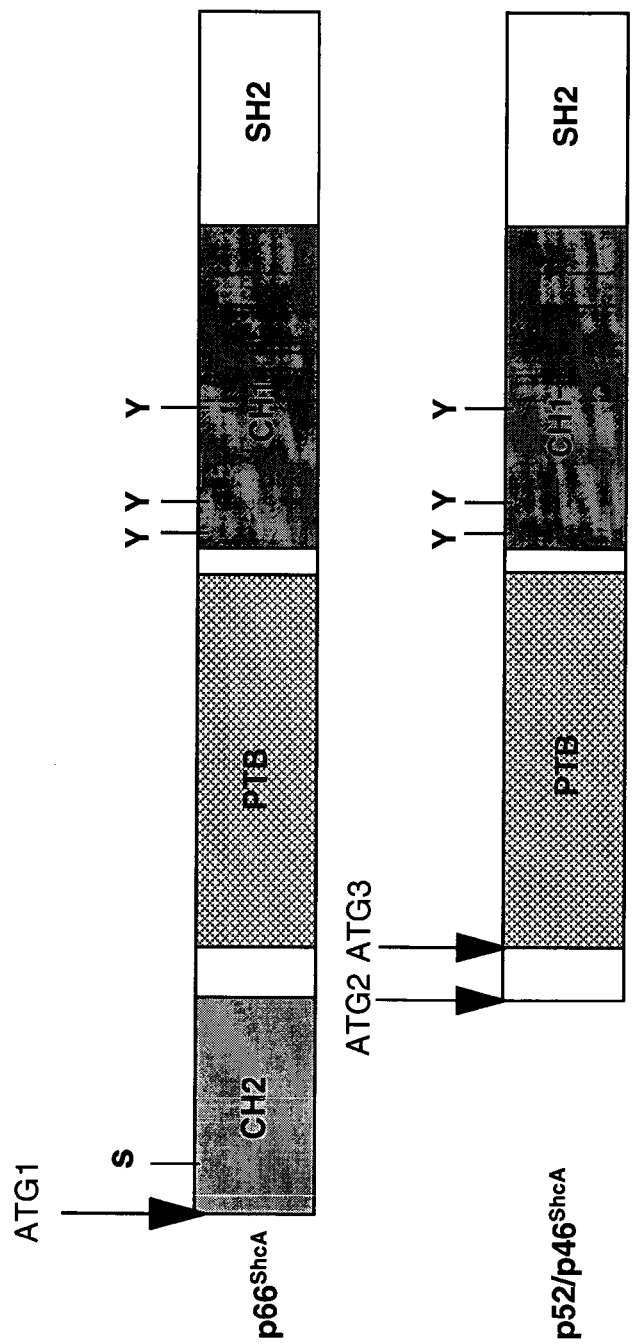
FIG. 1 is a cartoon representation depicting the organization of several ShcA proteins.

Many cellular proteins exert their function by interacting with other proteins in the cell. Examples of this are found in the formation of multiprotein complexes and the association of enzymes with their substrates. It is widely believed that a great deal of information can be gained by understanding individual protein-protein interactions, and that this is useful in identifying complex networks of interacting proteins that participate in the workings of normal cellular functions. The knowledge gained by characterizing these networks can lead to valuable insight into the causes of human diseases and can eventually lead to the development of therapeutic strategies. The yeast two-hybrid assay is a powerful tool for determining protein-protein interactions and it has been successfully used for studying human disease pathways. In one embodiment of this technique, a protein of interest (or a fragment of that protein) is expressed in a population of yeast cells that collectively contain all protein sequences introduced from a cDNA library of interest. Yeast cells that possess protein sequences that interact with the protein of interest are then genetically selected, and the identity of those interacting proteins is determined by DNA sequencing. Thus, proteins that can be demonstrated to interact with a protein known to be involved in a human disease are therefore also implicated in that disease.

In one aspect, the present invention relates to the discovery of novel interactions between at least the proteins described herein. The genes coding for some of the proteins might have been cloned previously, but their potential interaction in a physiological pathway or with a particular protein was unknown until the present disclosure.

In one aspect of the present invention, new protein-protein interactions have been discovered. The protein complexes comprising some of these interactions are set forth in Table 1, below.

TABLE 1

Protein Complexes of P66$^{shcA}$ and Prohibitin Interaction

| | |
|---|---|
| 1. | P66$^{shcA}$ and prohibitin |
| 2. | A fragment of P66$^{shcA}$ and prohibitin |
| 3. | P66$^{shcA}$ and a fragment of prohibitin |
| 4. | A fragment of P66$^{shcA}$ and a fragment of prohibitin |

The mechanism of regulation of mRNA expression of the shc locus been shown to be the result of two alternative promoters (Ventura et al., (2002) *J. Biol. Chem.* 277:22370–6) and variable initiation codon usage (Migliaccio et al., (1997) *E.M.B.O. J.* 16:706–16). The Shc family proteins have well defined protein domains that are evident in a number of adapter proteins (Migliaccio et al., (1997) *E.M.B.O. J.* 16:706–16), however the modular arrangement of these protein domains is unique and characteristic for this family (Migliaccio et al., (1997) *E.M.B.O. J.* 16:706–16; also see FIG. 1). In general, ShcA genes encode an amino-terminal phosphotyrosine-binding domain (PTB), followed by a central proline- and glycine-rich region (collagen homology domain-1 or CH1) containing distinct tyrosine phosphorylation sites, and terminating in a Src homology 2 (SH2) domain.

Molecular and biochemical evidence suggest a role for $p52/p46^{ShcA}$ in receptor tyrosine kinase (RTK)-mediated signal transduction and activation of the Ras/MAPK pathway, wherein the ShcA proteins are phosphorylated at distinct tyrosine residues in the CH1 domain, which brings into contact the activated RTKs and the Grb2 adapter protein (Migliaccio et al., (1997) *E.M.B.O. J.* 16:706–16; Downward, (1994) *F.E.B.S. Lett.* 338:113–17). The various ShcA domains mediate specific protein-protein interactions. ShcA binding to RTKs is mediated via the PTB and/or SH2 domains, while the SH2 domain alone is responsible for interacting with Grb2 (Migliaccio et al., (1997) *E.M.B.O. J.* 16:706–16). Grb2 is constitutively complexed with SOS, a ubiquitously expressed Ras guanine-nucleotide exchange factor (Downward, (1994) *F.E.B.S. Lett.* 338:113–17). Upon RTK activation, Shc/Grb2 complex formation leads to membrane translocation of SOS and subsequent activation of the Ras-MAPK pathway. In contrast to such biochemical evidence, ShcA–/– embryonic fibroblast cells derived from knockout mice show normal Ras activation, thereby calling into question the precise role of ShcA in the Ras/MAPK pathway (Bonfini et al., (1996) *Trends. Biochem. Sci.* 21:257–61).

The most recently defined member of the family, $p66^{ShcA}$ (encoded by SEQ ID NO:1) is an anomaly in the mitogenic activity of ShcA (Bonfini et al., (1996) *Trends. Biochem. Sci.* 21:257–61). The $p66^{ShcA}$ and $p52^{ShcA}/p46^{ShcA}$ proteins are encoded by two discrete transcripts. Codon initiation at the ATG1, 2 and 3 positions result in translation products, $p66^{ShcA}$, $p52^{ShcA}$ and $p46^{ShcA}$. FIG. 1 depicts the protein domains encoded by them and the organization of the domains relative to each other. In FIG. 1, "CH1" and "CH2" indicate collagen homology domains 1 and 2; "PTB" indicates phospho-tyrosine binding domain; "SH2" indicates Src homology 2 region; "S" represents the serine 36 phosphorylation site; and "Y" represents the tyrosine phosphorylation sites.

$p66^{ShcA}$ differs from the other two ShcA proteins ($p52/p46^{ShcA}$) in that it has a second proline/glycine-rich domain (CH2) at the amino-terminus that appears to confer different properties to this ShcA family member. $p66^{ShcA}$ is tyrosine-phosphorylated by RTKs and is not involved in Ras activation (Bonfini et al., (1996) *Trends. Biochem. Sci.* 21:257–61).

Various evidence suggests a role for $p66^{ShcA}$ in stress pathways activated by insults such as UV irradiation and oxidation (Migliaccio et al., (1999) *Nature* 402:309–13). For example, embryonic fibroblasts derived from mice null for the p66 protein (p66–/– MEFs) are resistant to oxidative stress ($H_2O_2$)-induced apoptosis, while ectopic expression of p66 renders the null MEFs sensitive to oxidative stress that leads to cell death (Migliaccio et al., (1999) *Nature* 402:309–13). Interestingly, ectopic expression of a point mutation of p66 (alanine substitution at serine 36 position) within the CH2 domain does not confer similar sensitivity to oxidative stress as the wild-type gene, implicating Ser36 as a critical amino acid necessary for sensing oxidative damage and concomitant outcome (Migliaccio et al., (1999) *Nature* 402:309–13). Serine 36 is phosphorylated in vitro when subjected to different stimuli such as oxidative stress (Migliaccio et al., (1999) *Nature* 402:309–13), insulin (Kao et al., (1997) *Endocrinol.* 138:2474–80), activation of endothelin-1 (Foschi et al., (2001) *J. Biol. Chem.* 276:26640–47), treatment with the phorbol ester TPA, and exposure to Taxol (El-Shemerly et al., (1997) *J. Biol. Chem.* 272:30599–602; Yang & Horwitz, (2000) *Cancer Res.* 60:5171–78). Mice null for the p66 gene show more tolerance to paraquat toxicity, an inducer of oxygen radicals, relative to wild-type mice (Migliaccio et al., (1999) *Nature* 402:309–13). This enhanced tolerance to free radicals correlates with prolonged life span in the null-mice and suggests a key role for $p66^{ShcA}$ in free radical-induced damage and life-span regulation (Migliaccio et al., (1999) *Nature* 402:309–13).

All of the ShcA protein domains (PTB, CH1 and SH2) that are defined so far interact with various cellular proteins, and have aided in determining the ShcA mechanism of action and biological significance. Pelicci and colleagues (Migliaccio et al., (1997) *E.M.B.O. J.* 16:706–16) showed that the CH2 domain may be a protein-protein interface, and the putative SH3 binding domains in this region bind PLCγ and $p120^{GAP}$ in vitro (Migliaccio et al., (1997) *E.M.B.O. J.* 16:706–16).

To ascertain the cellular relevance of this newly defined ShcA family member, an alternate approach (the yeast two-hybrid system) was employed in the present invention to determine the molecular partners of $p66^{ShcA}$ that interact within the CH2 domain. CH2-specific antibodies were generated to verify biochemical interaction with the candidate genes identified by the two-hybrid method and to establish its subcellular localization by indirect immunofluorescence. Green fluorescent tagged-protein expression was also used to determine subcellular localization in live cells. In various aspects of the present invention it was observed that $p66^{ShcA}$ is sequestered into mitochondria upon exposure to hydrogen peroxide, and that phosphorylation of ser36 is prerequisite for this event. Additionally, it was observed that a truncated $p66^{ShcA}$ protein, in which the PTB-CH1-SH2 region was deleted, and the CH2-GFP engineered protein were unable to induce mitochondrial import of the GFP reporter protein when challenged with peroxide. This data indicates the CH2 domain itself does not carry the necessary information for mitochondrial import of $p66^{ShcA}$.

Upon recruitment to mitochondria, $p66^{ShcA}$ is capable of interacting with the inner mitochoncirial membrane protein, prohibitin (encoded by SEQ ID NO:2). Prohibitin is a ubiquitously expressed, evolutionarily conserved protein (Tavernarakis et al., (1999) *Trends Biochem. Sci.* 24:425–27) implicated in a number of cellular events. Eukaryotic cells from yeast to mammals are strikingly similar in the mechanisms by which they execute basic cellular processes such as energy metabolism, cell cycle, DNA replication, and aging. Ranging from *Saccharomyces cerevisiae* to diploid human fibroblasts, prohibitins have been implicated in the regulation of replicative life span of cells and in the maintenance of mitochondrial morphology (Coates et al., (2001) *Exp. Cell Res.* 265:262–73).

Reports in the literature have suggested a role for prohibitin in the regulation of membrane protein degradation (Langer et al., (2001) *Biochem. Soc. Trans.* 29:431–36), regulation of gene expression (Wang et al., (1999) *Mol. Cell Biol.* 19:7447–60), regulation of cell cycle (Coates et al., (2001) *Exp. Cell Res.* 265:262–73), mitochondrial inheritance (Sutovsky et al., (2000) *Biol. Reprod.* 63:582–90), cellular immortalization (McClung et al., (1995). *Exp. Gerontol.* 30:99–124), senescence (Coates et al., (2001) *Exp. Cell Res.* 265:262–73) and tumor suppression (McClung et al., (1995). *Exp. Gerontol.* 30:99–124). Despite the apparent variability in its cellular role one accepted fact regarding prohibitin is its mitochondrial location, where it is specifically associated with the inner membrane (Langer et al., (2001) *Biochem. Soc. Trans.* 29:431–36).

One report on prohibitins suggests a direct chaperone function for the assembly of inner mitochondrial membrane proteins, such as the respiratory chain enzyme complexes (Coates et al., (2001) *Exp. Cell Res.* 265:262–73; Nijtmans et al., (2002) *Cell Mol. Life Sci.* 59:143–55), whose activity is particularly regulated in situations of mitochondrial stress. In another report, the prohibitin complex was found to transiently associate with cytochrome c oxidase subunits, Cox2p and Cox3p, the terminal complex of the respiratory chain enzyme complexes (Nijtmans et al., (2000) *E.M.B.O. J.* 19:2444–51). In view of the link between aging and oxidative stress response, prohibitins and mitochondrial function relative to the respiratory complexes, a prohibitin-$p66^{ShcA}$ interaction, which forms an embodiment of the present invention, can be employed in deciphering a role for $p66^{ShcA}$ in mitochondrial dysfunction during oxidative stress.

Improved tolerance to oxidative stress of $p66^{shcA-/-}$ mice indicates a role for $p66^{shcA}$ in stress response. Particularly, phosphorylation of $p66^{shcA}$ at serine 36 within the CH2-domain is critical to discern stress. In one aspect of the present invention, this was tested directly by employing the CH2-domain as bait, which led to the identification of the mitochondrial protein, prohibitin, which interacts with $p66^{shcA}$. Anti-$p66^{shcA}$ and anti-prohibitin antibodies demonstrated mitochondrial co-localization of the two proteins in peroxide-challenged fibroblasts. Cell fractionation studies showed preferential segregation of phosphorylated-$p66^{shcA}$ with mitochondria. Expression of epitope-tagged $p66^{shcA}$ and two point mutants (S36A, S36D) revealed the unambiguous sequestration of only wild-type protein into mitochondria when stressed and concomitant mitochondrial depolarization. These data show a functional link between $p66^{shc}$ phosphorylation and its mitochondrial sequestration, which induces mitochondrial dysfunction and cell death. The data presented in the instant disclosure support a substantial role for serine36 phosphorylation in $p66^{ShcA}$ mitochondrial import and a role for the phospho-protein in the deregulation of mitochondrial membrane potential and function.

In unstimulated NIH3T3 fibroblasts (Lotti et al., (1996) *Mol. Cell Biol.* 16:1946–54) and HeLa cells (Oksvold et al., (2000) *J. Histochem. Cytochem.* 48:21–33) the ShcA proteins localize on the membranes of the endoplasmic reticulum and, upon stimulation with EGF, there is a distinct redistribution of the protein to the cytosolic surface of the plasma membrane and endosomes, keeping with its role as an adapter protein in growth factor induced RTK-ShcA-Grb2-Sos complex formation and signal transduction.

It has been reported that both during UV irradiation and paclitaxel treatment, the amount of $p66^{ShcA}$ isoform associated with Grb2 is significantly reduced relative to that observed during growth factor stimulation (Yang & Horwitz, (2000) *Cancer Res.* 60:5171–78). The differential sequestration of significant amounts of ShcA and its accumulation in mitochondria, specifically the p66 isoform during oxidative stress provide an explanation for the attenuation in the ShcA-Grb2 complex formation during situations of stress as opposed to growth factor stimulation. This differential distribution may be partially responsible for the shift in equilibrium from cell growth to cell death signaling during stress. The sequestration by mitochondria is regulated by phosphorylation of serine36 within the $p66^{ShcA}$-CH2 domain.

The general concept of a chaperone mediated mechanism of mitochondrial import of $p66^{ShcA}$ comes from the finding of a signaling complex between $p66^{ShcA}$ and 14-3-3 protein (see, e.g., Foschi et al., (2001) *J. Biol. Chem.* 276:26640–47). Their interaction may play a role in the regulation of $p66^{ShcA}$ entry into mitochondria. Until recently, 14-3-3 proteins were thought to be present only in the cytoplasm and on the plasma membrane. However, the recent illustration of 14-3-3 proteins in the stroma of plant chloroplasts (Sehnke et al., (2000) *Plant Physiol.* 122: 235–42), and in the inner mitochondrial-membrane compartment (Bunney et al., (2001). *Proc. Natl. Acad. Sci. U.S.A.* 98:4249–54) implies a new role for the protein. de Boer and colleagues (Bunney et al., (2001). *Proc. Natl. Acad. Sci. U.S.A.* 98:4249–54) found 14-3-3 proteins to be associated with mitochondrial and chloroplast ATP synthases, key enzymes in energy metabolism, through direct interaction with the F (1) beta-subunit. This association results in drastically reduced activity of the ATP synthases and the metabolic processes in plants (Bunney et al., (2001). *Proc. Natl. Acad. Sci. U.S.A.* 98:4249–54). Taken together, these observations suggest that 14-3-3 proteins may chaperone phosphorylated $p66^{ShcA}$ into mitochondria, where in a complex with prohibitin alters mitochondrial membrane potential and function.

Pelicci and colleagues (Migliaccio et al., (1999) *Nature* 402:309–13) have demonstrated that serine 36 phosphorylation is necessary for normal stress response that results in oxidative damage and apoptosis (Migliaccio et al., (1999) *Nature* 402:309–13), however the precise role of this phosorylation event was not defined. Only recently, it has been shown that the stress-activated protein kinases (SAPKs), also called c-Jun N-terminal kinases (JNKs), are responsible for $p66^{ShcA-ser36}$ phosphorylation in response to UV irradiation (Le et al., (2001) *J. Biol. Chem.* 276:48332–36). JNKs are an essential part of the signaling mechanism that elicits stress response by injured cells, and these cytoplasmic kinases are activated upon a variety of external insults such as, UV irradiation, hypoxia, and heavy metal toxicity that result in DNA damage and apoptosis (Pearce & Humphrey, (2001) *Trends Cell Biol.* 11:426–33). Recent evidence suggests that the forkhead transcription factor, FKHRL1 is regulated in a redox dependent manner and require $p66^{ShcA}$ signaling (Nemoto & Finkel, (2002) *Science* 295:2450–52). Nemoto & Finkel observed that the level of intracellular hydrogen peroxide is significantly increased (>10 fold) in wild-type $p66^{ShcA}$ cells relative to $p66^{ShcA-/-}$ cells when subjected to a mild stressor such as serum starvation (Nemoto & Finkel, (2002) *Science* 295: 2450–52). One of the mechanisms of $p66^{ShcA}$ induced apoptosis involves both p53 and p21 stress response genes whose activity is impaired in the $p66^{ShcA-/-}$ null mice (Migliaccio et al., (1999) *Nature* 402:309–13).

In one aspect, the present invention discloses the observation that the CH domains of ShcA proteins are capable of interacting with the inner mitochondrial membrane protein prohibitin. The present invention also establishes redistribution of the $p66^{ShcA}$ isoform within the cell upon peroxide challenge and that it is preferentially sequestered into mitochondria. The present invention also demonstrates that mitochondrial targeting of $p66^{ShcA}$ during stress is orchestrated by the phosphorylation of serine 36 within the CH2 domain, that this modification is necessary, and that amino acid substitutions at this site result in misdirected localization of the mutant proteins. Anti-$p66^{ShcA}$ specific antibodies confirm mitochondrial localization of endogenously expressed protein and its co-localization with prohibitin in normal fibroblasts only when subjected to peroxide challenge.

The data disclosed herein establish a direct consequence of the mitochondrial import of phosphorylated $p66^{ShcA}$ and its association with prohibitin, and a potential function for the prohibitin-$p66^{ShcA}$ complex in the mitochondrial membrane depolarization process that governs metabolic events such as, bioenergetics and free radical formation.

Since the interactions described herein are involved in a physiological pathway, the identification of agents which are capable of modulating the interaction will provide agents that can be used to track the physiological disorder or to use as lead compounds for development of therapeutic agents. An agent may modulate expression of the genes of interacting proteins, thus affecting interaction of the proteins.

EXAMPLES

The present invention is further detailed in the following examples, which are offered by way of illustration alone and are not intended to limit the invention in any manner. Standard techniques well known to those skilled in the art, or the techniques specifically described below, are utilized.

Example 1

Cell Culture

HeLa, NIH3T3 and HEK 293 cells were obtained from American Type Culture Collection. All cells were maintained in Dulbecco's Modified Eagle's medium (DMEM) (Life Technologies, Inc.) supplemented with 10% fetal bovine serum, 100 units/ml penicillin and 100 µg/ml streptomycin at 37° C. in a 95% air 5% $CO_2$ humidified incubator.

Example 2

Molecular Cloning and Sequencing

Two PCR primer sets were designed based on the published sequence for human $p66^{ShcA}$ CH1 and CH2 domains. Oligonucleotide sets (1a)5'-CATATGGAGCCACCTGAC-CATCAGTACTATAATG-3' (SEQ ID NO:3) and (1b) 5'-GAATTCTCA GGGCTCCCCTCGGAGCTGCTC-3' (SEQ ID NO:4) and (2c) 5'-CATATGGATCTCCTGC-CCCCCA AGCCC-3' (SEQ ID NO:5) and (2d) 5'-GAAT-TCTCAGTCCTGGAGGAGGGGTAGGGG (SEQ ID NO:6) were used to amplify the CH1 and CH2 domains respectively. The engineered NdeI and EcoRI restriction enzyme sites are underlined. PCR amplification was performed using Advantage-GC cDNA PCR Kit (Clontech) along with HeLa cell cDNA as a template. The PCR products were subcloned into the TA vector (Invitrogen) for sequence analysis, then subcloned into pGBKT7 vector (bait plasmid) from the Matchmaker GAL4 Two-Hybrid System 3 (Clontech). Point mutations in the CH2 domain were generated using a mutagenesis kit (Promega).

Example 3

Yeast Two-Hybrid Screening

A commercially available HeLa cDNA library (Clontech Matchmaker Library) constructed in pACT2 containing the sequence encoding the GAL4 activation domain was used to screen AH 109 yeast strain transfected with the CH1, CH2 or null bait plasmids. $1.5 \times 10^6$ transformants were selected on low stringency (SD/-Leu/-Trp) plates (Clontech). A representative number of colonies from the SD/-Leu/-Trp plates were then replica plated onto medium stringency (SD/-His/-Leu/Trp/X-α-gal) and high stringency (SD/-Ade/-His/-Leu/-Trp/X-α-gal) plates for 4–7 days at 30° C. The blue colonies from medium stringency plates that contained both the bait and interacting targets were PCR amplified by using Matchmaker AD LD-Insert screening amplimers. The PCR products were further analyzed by DNA sequencing and searched against the Genebank database. Clones identified by this method were verified for interaction specificity. At the time of verification, p53 and SV40 large T-antigen were used as positive controls, and pGBKT7-Lam as a negative control for all interaction specificity assays.

Example 4

Mammalian Expression Plasmid Construction

The $p66^{ShcA}$ cDNA was generated using RT-PCR based methods. Polynucleotides encoding wild type $p66^{ShcA}$ (SEQ ID NO:1) and point mutations $p66^{ShcA}$ (S36A) (SEQ ID NO:7) and $p66^{ShcA}$ (S36D) (SEQ ID NO:8) were cloned into pEGFP-N1 (Clontech) vector where the Green Fluorescent Protein-tag is at the C-terminal end of the chimeric protein. GFP-$p66^{ShcA}$, S36A and S36D were transfected into HEK293 cells using Lipofectin (GIBCO BRL). Stable expression colonies were selected using G418 and were screened for expression by western blotting using anti-GFP antibody (Clontech). Localization of GFP chimeric proteins in live cells was visualized using a confocal microscope.

Example 5

$p66^{ShcA}$ Antibody Generation

The anti-$p66^{ShcA}$ specific polyclonal antibody was raised against the CH2 region. The region encoding amino acids 1–110 was isolated using PCR based methods and cloned into bacterial pGEX-2TK vector. GST-$p66^{ShcA}$CH2 recombinant protein was purified using Glutathione Sepharose following manufacturer's instructions (Promega). Protein was further purified by SDS-PAGE to eliminate GST contamination. Immunizing New Zealand White rabbits with GST-$p66^{ShcA}$CH2 containing SDS-gel fragments generated a polyclonal anti-$p66^{ShcA}$ serum.

Example 6

Immunoprecipitation and Western Blot Analysis

HeLa cells were cultured under low serum conditions and treated with 100 µM $H_2O_2$ for 4 hours. Cell fractionation was done according to manufacture's protocol (Clontech). For immunoprecipitation, treated and untreated cells were solubilized in RIPA buffer (25 mM Tris, pH 7.4, 150 mM KCl, 5 mM EDTA, 1% Nonidet P-40, 0.5% sodium deoxycholate, and 0.1% SDS) supplemented with commercially prepared protease inhibitor cocktail (BioRad). Whole cell lysates were precleared with 20 µl of protein G-agarose beads. Precleared whole-cell extracts were incubated with 5 µl of anti-prohibitin antibody (NeoMarkers) overnight at 4° C. Immune complexes were adsorbed on protein G-agarose beads. The resulting beads were washed 5 times with cold RIPA buffer and proteins were eluted and denatured by heating for 3 minutes at 95° C. in reducing Laemmli buffer. Samples were resolved by SDS-PAGE (4–20% gradient), and immobilized on nitrocellulose membrane for Western blot analysis. Immunoblot analysis of whole cell protein or immunoprecipitated complexes were done using anti-ShcA (1:400; Santa Cruz), anti-ERK1 (1:400; Santa Cruz) or anti-Prohibitin (1:400; NeoMarkers) antibodies, and detected with horseradish peroxidase-conjugated species specific secondary antiserum (Bio-Rad Laboratories) or with HRP conjugated anti-rabbit IgG F (ab')$_2$ antibody (Pierce).

Example 7

Indirect Immunofluorescence

NIH3T3 cells were grown in chamber slides and treated with 100 μM $H_2O_2$ for 4 hours. Cells were washed 2× in PBS (phosphate buffered saline, pH 7.5) and fixed in cold methanol for 5 min at −20° C. The fixed cells were air dried for 30 minutes and permeabilized in PBS+0.5% Triton X-100 for 30 min at room temperature. Primary Anti-p66$^{ShcA}$ specific serum (1:1,000) and commercially available anti-prohibitin (1:250) monoclonal antibodies (NeoMarkers) were added to the chamber-slide wells and incubated at 37° C. for 1 h in a humid chamber followed by washing in PBS. Secondary rabbit or anti-mouse antibodies conjugated with rhodamine or fluorescine (Pierce) were used for detecting p66$^{ShcA}$ and prohibitin respectively. Localization was visualized and documented using a confocal microscope.

Example 8

$\Delta\psi_m$ Anlysis by Flow Cytometry

Two sets of pEGFP, p66$^{ShcA}$-GFP and p66$^{ShcA}$ mutants (S36A and S36D) stable cell lines expressing green fluorescence protein (GFP) as a reporter were cultured in growth medium for 24 hours. One set of cell lines was maintained in growth medium for 24 hours and tested with 100 uM $H_2O_2$ for four hours, parallel controls were included. At the end of the treatment period, cells were rinsed in PBS and trypsinized and stained with 5 uM tetramethylrosamine chloride (exc.: 488 nm; em: 565–592; TMR-chloride from Molecular Probes), in D-MEM medium (phenol red free) and incubated for 30 minutes. Cells were washed and re-suspended in fresh D-MEM medium (phenol red free) for data acquisition by a FACS Calibur flow cytometer, (Becton Dickinson) with a 488 nm wavelength excitation laser and emission collected through a band pass filter 525+−20 nm for the GFP and a 575+−20 nm band pass filter for the TMR-Cl; appropriate compensation was applied. The data collection was done using Cellquest from BD and analysis using Flow Jo software from Tree Star Inc.

Example 9

Identification of a p66$^{ShcA}$ Interacting Protein

Figure 2:
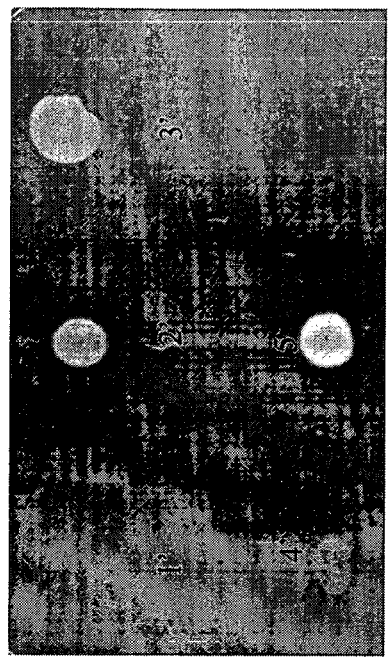
FIG. 2 is a series of photographs depicting the interaction of the $p66^{ShcA}$-CH2 domain with prohibitin by the yeast two-hybrid method. Representative colonies (left panel, identified as 1, 2, 3, 4, and 5) formed on a low stringency selection plate (SD-Leu/-Trp) were replica plated (right panel, identified as 1', 2', 3', 4' and 5') respectively onto a high stringency (SD/-Ade/-His/-Leu/-Trp/X-α-Gal) selection plate and positive interaction between two proteins was detected using growth and X-α-Galactosidase on the high stringency plate.
Figure 2:
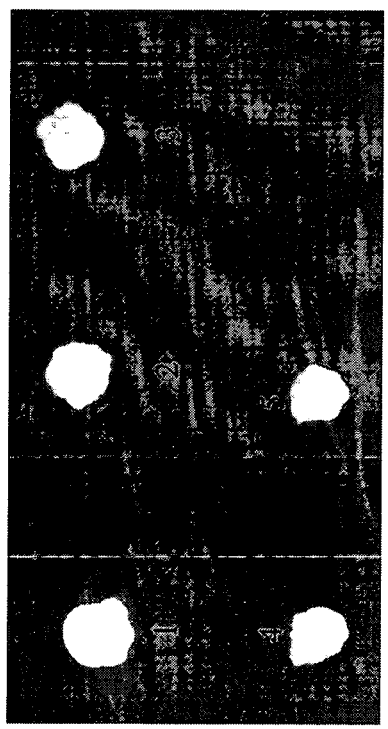

A HeLa cDNA library was screened in a yeast two-hybrid interaction assay using the p66$^{ShcA}$-CH2 domain as bait (FIG. 1). From 1.5×10$^6$ transformants, several clones that interact with the CH2 domain and not with null bait plasmid were isolated. Among them, a clone encoding the mitochondrial protein prohibitin (PHB), was isolated (FIG. 2). Since an association between p66$^{ShcA}$ and mitochondria may be important for its function during oxidative stress, the binding between the CH2 domain and prohibitin was further characterized.

TABLE 2

Plasmid Combinations Used in Yeast Two-hybrid Analyses

| No. | Plasmid Combination | SD/-Leu/-Trp | SD/-Ade/-His/-Leu/-Trp/X-α-Gal |
|---|---|---|---|
| 1 | Null Vector + PHB | growth | No growth |
| 2 | CH2 (WT, S36) + PHB | growth | growth/blue |
| 3 | CH2 (MT, S36A) + PHB | growth | growth/blue |
| 4 | CH2 (MT, S36D) + PHB | growth | growth/blue |
| 5 | p53 + SV 40 TAg | growth | growth/blue |

Serine phosphorylation within the CH2 domain at position 36 has been implicated in oxidative stress response (Migliaccio et al., (1999) *Nature* 402:309–13). To address the significance of serine36 posttranslational modification, two amino acid substitutions were made in which serine 36 was replaced with an alanine (S36A; encoded by SEQ ID NO:7) to mimic a non-phosphorylatable residue, or with an aspartate (S36D; encoded by SEQ ID NO:8) to mimic a constitutively-phosphorylated serine. The modified baits were tested for interaction with prohibitin in a small-scale interaction trap assay (FIG. 2). It was found that both of the CH2 point mutants were capable of interacting with prohibitin as efficiently as wild-type, suggesting that the interaction is not influenced by serine at this position and that the interaction between the CH2 domain and prohibitin is not dependent on serine 36 phosphorylation or by the presence of a negatively charged amino acid at this position.

Example 10

In Vitro Interaction of p66$^{ShcA}$ with Prohibitin

To confirm the interaction of p66$^{ShcA}$ with prohibitin, immunoprecipitation was performed with anti-PHB serum followed by anti-ShcA immunoblot analysis using commercially available antibodies. The anti-ShcA antibody is a rabbit polyclonal serum generated against the SH2 domain common to all three ShcA proteins, while the anti-PHB monoclonal antibody is highly specific for prohibitin. Expression of p66$^{ShcA}$ has been documented in a number of tumor cell lines (Migliaccio et al., (1997) *E.M.B.O. J.* 16:706–16; Jackson et al., (2000) *Clin. Cancer Res.* 6:1135–39), and it was determined that HeLa and HEK293 cells constitutively express detectable levels of all three ShcA proteins by western blotting using the anti-ShcA-SH2 antibody.

Figure 3:
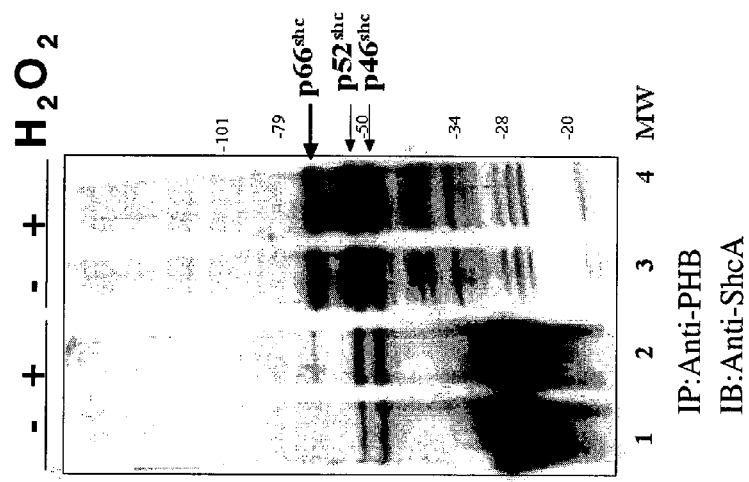
FIG. 3 is a photograph of a SDS-PAGE gel depicting the co-precipitation of ShcA family proteins with prohibitin.
Figure 4:
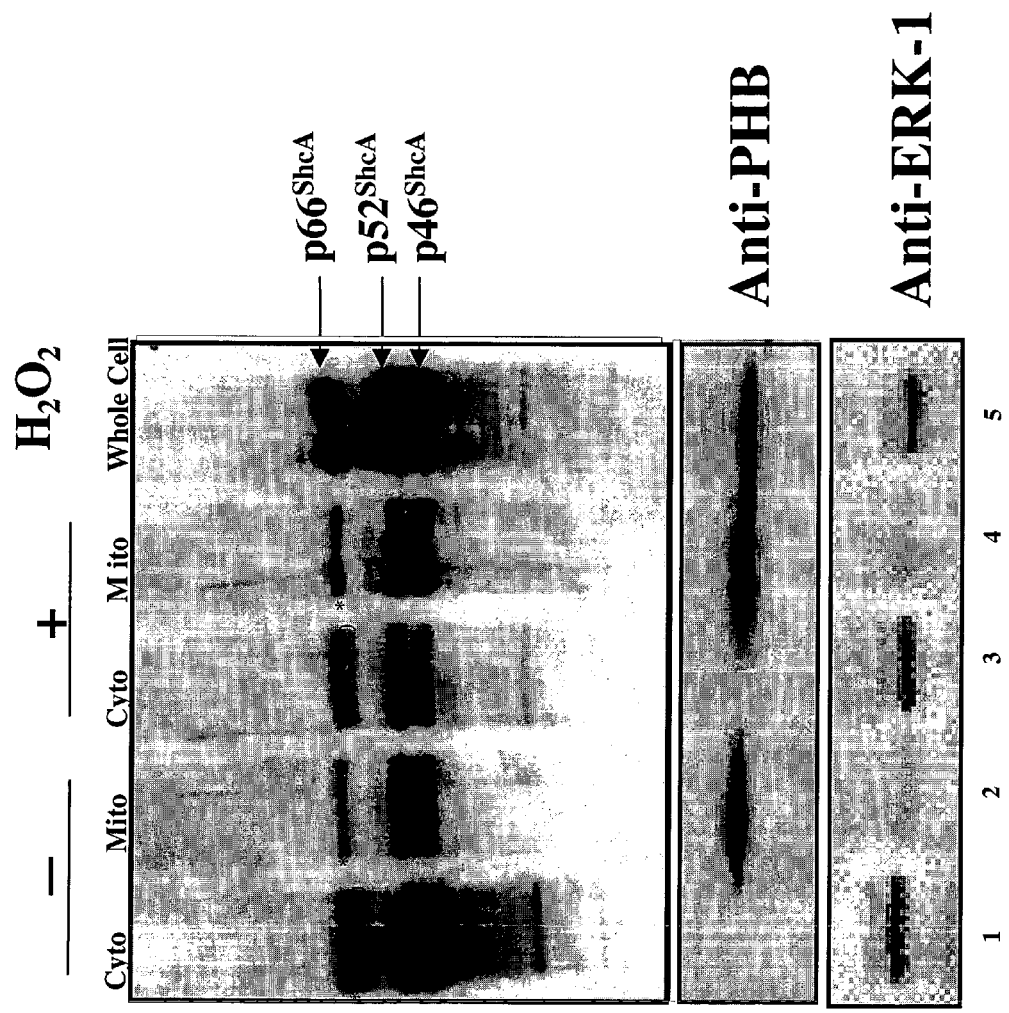
FIG. 4 is a photograph depicting the finding that serine-phosphorylated $p66^{ShcA}$ and $p52^{ShcA}/p46^{ShcA}$ proteins are present in cellular fractions enriched in mitochondria.

FIG. 3 illustrates HeLa cell lysates (Lanes 3 and 4) prepared from cell that were untreated (−) and treated (+) with hydrogen peroxide ($H_2O_2$) were immunoprecipitated (IP) with anti-prohibitin (Anti-PHB) mouse monoclonal antibodies followed by immunoblot (IB) analysis (lanes 1 and 2) using anti-ShcA rabbit polyclonal antibody (Anti-ShcA-SH2 domain). Arrows to the right indicate the three ShcA protein isoforms that co-precipitate with the anti-prohibitin antibody complex. Shown along one side are the Molecular Weight protein standards (MW). Both cell lines were also confirmed for endogenous prohibitin expression using anti-prohibitin antibodies (FIG. 4).

HeLa cell lysates were used to verify the in vitro interaction of endogenously expressed p66$^{ShcA}$ with prohibitin. Cells were cultured under low serum conditions with and without $H_2O_2$ for 4 hours, and whole cell lysates were prepared for immunoprecipitation using the anti-prohibitin monoclonal antibody. The immuno-precipitated complex and the total initial material were analyzed by western blotting using anti-ShcA-SH2 antibodies (FIG. 3). Clearly visible in FIG. 3, lane 2 is p66$^{ShcA}$ in the $H_2O_2$ treated sample. It was found that p46$^{ShcA}$ and p52$^{ShcA}$ also co-precipitate with prohibitin. There appears to be a visible increase in the amount of all three ShcA proteins that co-precipitate with PHB upon treatment with H$_2$O$_2$ (equal amount of input material was used for IP and is shown FIG. 3, lanes 3 and 4). Subsequent to this observation, the CH1 domain was tested for interaction with prohibitin using the yeast two-hybrid assay; it was found that the CH1 domain is also capable of interacting with prohibitin.

Example 11

Biochemical Localization of p66$^{ShcA}$ in Mitochondria

To establish mitochondrial localization of p66$^{ShcA}$, p52$^{ShcA}$, p46$^{ShcA}$ and prohibitin both cell fractionation and indirect immunofluorescence analyses were performed. The anti-ERK-1 and anti-prohibitin antibodies were used to demonstrate purity of the mitochondrial and cytoplasmic fractions. HeLa cells grown and treated with or without H$_2$O$_2$ were harvested, and differential centrifugation methods were used to fractionate cytoplasm- and mitochondria-enriched preparations. The enriched fractions were solubilized in loading buffer containing SDS and DTT and subjected to SDS-PAGE followed by immunoblotting, using anti-ShcA, anti-PHB and anti-ERK-1 antibodies.

Shown in FIG. 4 is a compilation of western blots from one such experiment: HeLa cell lysates (Lanes 5) prepared from cells that were untreated (−) or treated (+) with hydrogen peroxide (H$_2$O$_2$) were fractionated upon hypotonic disruption using differential centrifugation methods into mitochondria enriched (Mito; lanes 2 and 4) and cytoplasm enriched (cyto; lanes 1 and 3) fractions. Samples were analyzed by western blotting using the anti-ShcA (top), anti-prohibitin (center) and anti-ERK-1 (bottom) antibodies. Arrows: the three ShcA protein isoforms; asterisks: serine36-phosphorylated-p66$^{ShcA}$ protein; crescent: non-phosphorylated serine36-p66$^{ShcA}$ protein.

All three ShcA protein isoforms are constitutively present in HeLa cell cytoplasm and mitochondria (see FIG. 4, lane 1 and 2). However, there appears to be an increase in all three ShcA proteins in the mitochondria relative to the cytoplasm in cells treated with H$_2$O$_2$ (see FIG. 4, lane 2 and 4). In the case of p66$^{ShcA}$, there appear to be two forms clearly visible by SDS-PAGE, a slow-(*) and fast-( )) migrating form of the protein. In the cytoplasm (see FIG. 4, lane 1 and 3), both the slow- and fast-migrating forms are apparent, while in the mitochondria only the slow-migrating form of the protein is present (see FIG. 4, lane 2 and 4). The slower-migrating version represents the p66$^{ShcA}$ serine36 phosphorylated protein (Migliaccio et al., (1999) *Nature* 402:309–13; Yang & Horwitz, (2000) *Cancer Res.* 60:5171–8), and it appears to be differentially recruited into mitochondria. A substantial amount of this variant of p66$^{ShcA}$ is also visible in the cytoplasm, suggesting that serine 36 phosphorylation may occur via a kinase in the cytoplasm and that phosphorylation may play a critical role in p66$^{ShcA}$ import into mitochondria.

Example 12

Generation of p66$^{ShcA}$ Specific Antibodies

In order to determine the subcellular localization of p66$^{ShcA}$, we generated polyclonal antibodies against the unique CH2 domain. Bacterially-generated GST-CH2 recombinant protein was used as an antigen to immunize rabbits that yielded very high titer p66$^{ShcA}$ specific antibody.

Figure 5A:
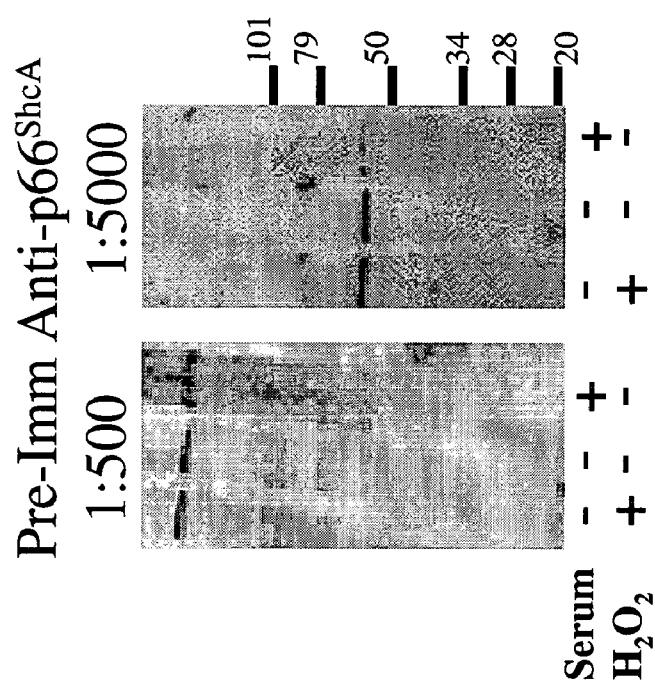
FIG. 5A is a photograph depicting the specificity of anti-$p66^{ShcA}$ antibodies by western blotting and prohibitin co-localization.
Figure 5B:
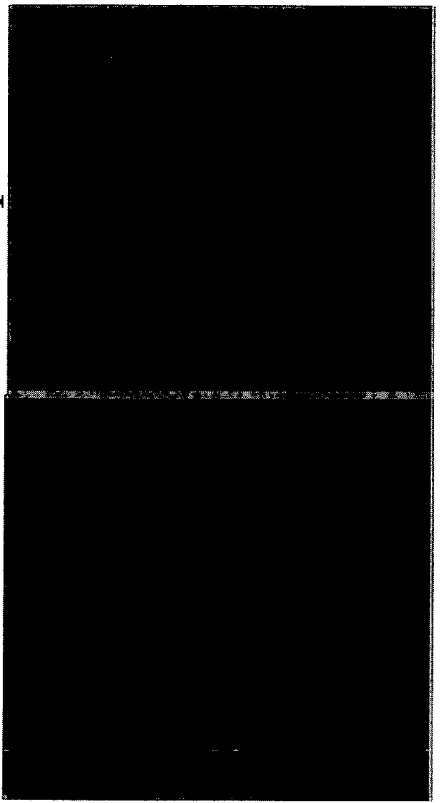
FIG. 5B is a series of photographs depicting the indirect immunofluorescence detection of $p66^{ShcA}$.
Figure 5B:
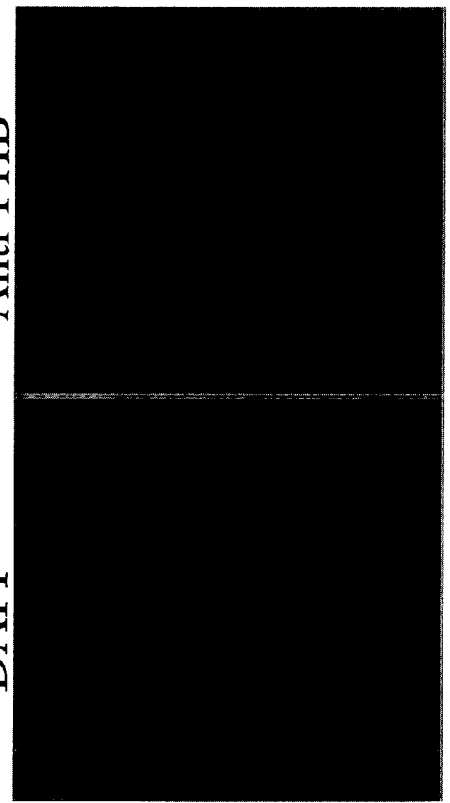
Figure 5C:
FIG. 5C is a photograph depicting the immunofluorescence detection of prohibitin co-localization.

Shown in FIGS. 5A–5C are the results from pre-immune and anti-p66$^{ShcA}$ specific antibodies tested for immunoreactivity against lysates prepared from mouse embryonic fibroblasts (NIH 3T3); control cells (grown in DMEM+10% serum), serum-deprived cells (serum starvation for 14 hours) and serum-deprived cells subjected to subsequent oxidative stress (serum starvation+H$_2$O$_2$). In western blots, pre-immune serum shows no visible immunoreactivity in the region of interest (50–70 kDa). However, the p66$^{ShcA}$-immune serum shows specific reactivity to a single band between the 50 and 70 kDa molecular weight markers that is approximately 66 kDa in size Turning now to FIG. 5A, HeLa cell lysates were prepared as indicated. Shown on the left is the pre-immune blot (Pre-Imm.) that reveals a non-specific immuno-reactive band well over 101 kDa and is present in HeLa lysates prepared from all three treatment conditions. The panel on the right of FIG. 5A shows the results from the immune serum (Anti-p66$^{ShcA}$). A single immuno-reactive band over 50 kDa, and smaller than the 79 kDa molecular weight standard is clearly visible.

Turning next to FIG. 5B, HeLa cells were stained using the anti-p66$^{ShcA}$ (Panel B) and anti-prohibitin (Panel D) antibodies. The cells were also stained with DAPI (Panels A and C).

FIG. 5C depicts the co-localization (indicated by arrows) of anti-p66$^{ShcA}$ with anti-prohibitin antibodies suggests that the two proteins (yellow bodies) coexist in close proximity to one another. The staining of short rod shaped structures (mitochondria) immediately surrounding the nucleus with both antisera is noted.

Control NIH 3T3 cells grown in the presence of serum show very low levels of p66$^{ShcA}$ expression, while stresses such as serum deprivation or serum deprivation coupled with peroxide challenge result in upregulation of p66$^{ShcA}$ expression. The exceptional specificity of the p66$^{ShcA}$ antibodies encouraged us to examine the localization of endogenously expressed p66$^{ShcA}$ in NIH 3T3 cells.

Example 13

Immuno-Localization of p66$^{ShcA}$ in Mitochondria

To determine the subcellular localization of p66$^{ShcA}$, indirect immunofluorescence using the p66$^{ShcA}$ specific antibody and rhodamine-conjugated secondary antibodies was employed to visualize its localization in mouse embryonic fibroblasts (NIH 3T3) treated with H$_2$O$_2$ for 4 hours. Prohibitin, a bona fide mitochondrial protein, was visualized using anti-prohibitin monoclonal antibodies and fluorescine-conjugated secondary antibodies (FITC). The DNA intercalating dye, DAPI, was used to stain nuclei. Images were captured using a confocal microscope. Representative cells stained with anti-p66$^{ShcA}$ or anti-prohibitin antibodies are shown in FIG. 5B. Cells show visible levels of both p66$^{ShcA}$ and prohibitin expression in the cytoplasm and, at this magnification (40×), both proteins show a reticular staining pattern in the cytoplasm. Marginal p66$^{ShcA}$ staining is evident in the nucleus (FIG. 5B). Interestingly, when NIH 3T3 cells were stained with both p66$^{ShcA}$ and prohibitin antibodies simultaneously, high magnification (100× times 2) revealed the co-localization of the two proteins (FIG. 5C). Simultaneous visualization of the DAPI, p66$^{ShcA}$ and prohibitin localization is made possible by overlay imaging technology (see, FIG. 5C, co-localization). Wherever p66$^{ShcA}$ and prohibitin co-localization is present it appears yellow in color (indicated by arrows in FIG. 5C). Mitochondria immediately surrounding the nucleus are stained with both anti-p66$^{ShcA}$ and anti-prohibitin antibodies (bodies indicated by arrows in FIG. 5C). Aside from the mitochondria that are positively stained for both proteins, there is a small percentage of p66$^{ShcA}$ and prohibitin positive bodies that do not show co-localization of the two proteins. It is likely that the purely p66$^{ShcA}$ positive bodies may be endosomes, known to contain p66$^{ShcA}$ associated with activated RTKs that are internalized upon receptor activation (Lotti et al., (1996) *Mol. Cell Biol.* 16:1946–54). The DAPI stained nucleus also shows some punctate anti-p66$^{ShcA}$ and anti-prohibitin staining. The mitochondrial localization of p66$^{ShcA}$ by indirect immunofluorescence and corroborative findings from cell fractionation analysis led us to investigate the role of phosphorylation in mitochondrial sequestration of the protein.

Example 14

Phosphorylation at Serine 36 is Necessary for Mitochondrial Targeting

The 14-3-3 family of proteins (a phospho-serine motif interacting protein) are regulators of a growing list of proteins e.g., BAD (Masters et al., (2001) *Mol. Pharmacol.* 60:1325–31). A recent report on serine phosphorylated-p66$^{ShcA}$ interaction with the protein 14–3–3 (Foschi et al., (2001) *J. Biol. Chem.* 276:26640–47), suggests close regulation of p66$^{ShcA}$ activity in cells upon serine phosphorylation. Since the p66$^{ShcA}$ primary amino acid sequence does not display a mitochondrial target sequence, it is conceivable that it is imported into mitochondria by a chaperone-mediated mechanism. To date, only serine 36 has been implicated in p66$^{ShcA}$ function (Migliaccio et al., (1999) *Nature* 402: 309–13).

In order to determine the biological significance of phosphorylation at serine 36 and investigate a possible role in p66$^{ShcA}$ mitochondrial targeting, a series of green fluorescent protein (GFP) chimeras were generated. The EGFP tag was added at the C-terminal end of p66$^{ShcA}$ to avoid artifacts due to improper protein folding and interference with the formation of key protein-protein interactions at the N-terminal end. GFP chimeras of full-length p66$^{ShcA}$ wild-type and two point mutants (i.e., S36A and S36D) were stably transfected into human embryonic kidney (HEK293) and human adult kidney (HK2) cells. The HEK293 cells exhibited endogenous p66$^{ShcA}$ expression and the HK2 cells showed no detectable levels of p66$^{ShcA}$ expression by western blot. This pair of cell lines (HEK293 and HK2) facilitated the analysis of p66$^{ShcA}$ expression outcome in a plus and minus endogenous p66$^{ShcA}$ expression background.

At the end of the selection period, stable expression clones were identified and isolated for all three p66$^{ShcA}$ constructs in HEK293 cells as well as for the GFP vector control. In case of HK2 cells, colonies were identified and isolated for both the p66$^{ShcA}$ mutants and the GFP vector, and no visible colony formation was observed with the p66$^{ShcA}$ wild-type plasmid. Although it is not the inventor's desire to be bound to any theory of operation, it was believed that constitutive expression of the p66$^{ShcA}$ gene product in normal HK2 cells causes severe growth suppression and absence of colony formation. Due to this fact, only the HEK293 cells were further investigated with regard to p66$^{ShcA}$ localization in the absence and presence of peroxide challenge.

Stable expression clones were screened using anti-GFP antibodies by western blotting and clones expressing comparable levels of the recombinant protein were analyzed further. Cells were grown on chamber slides and GFP localization was visualized in live cells using a confocal microscope. The dye, MitoTracker-Red® (Molecular Probes), was used to discern mitochondria.

Figure 6:
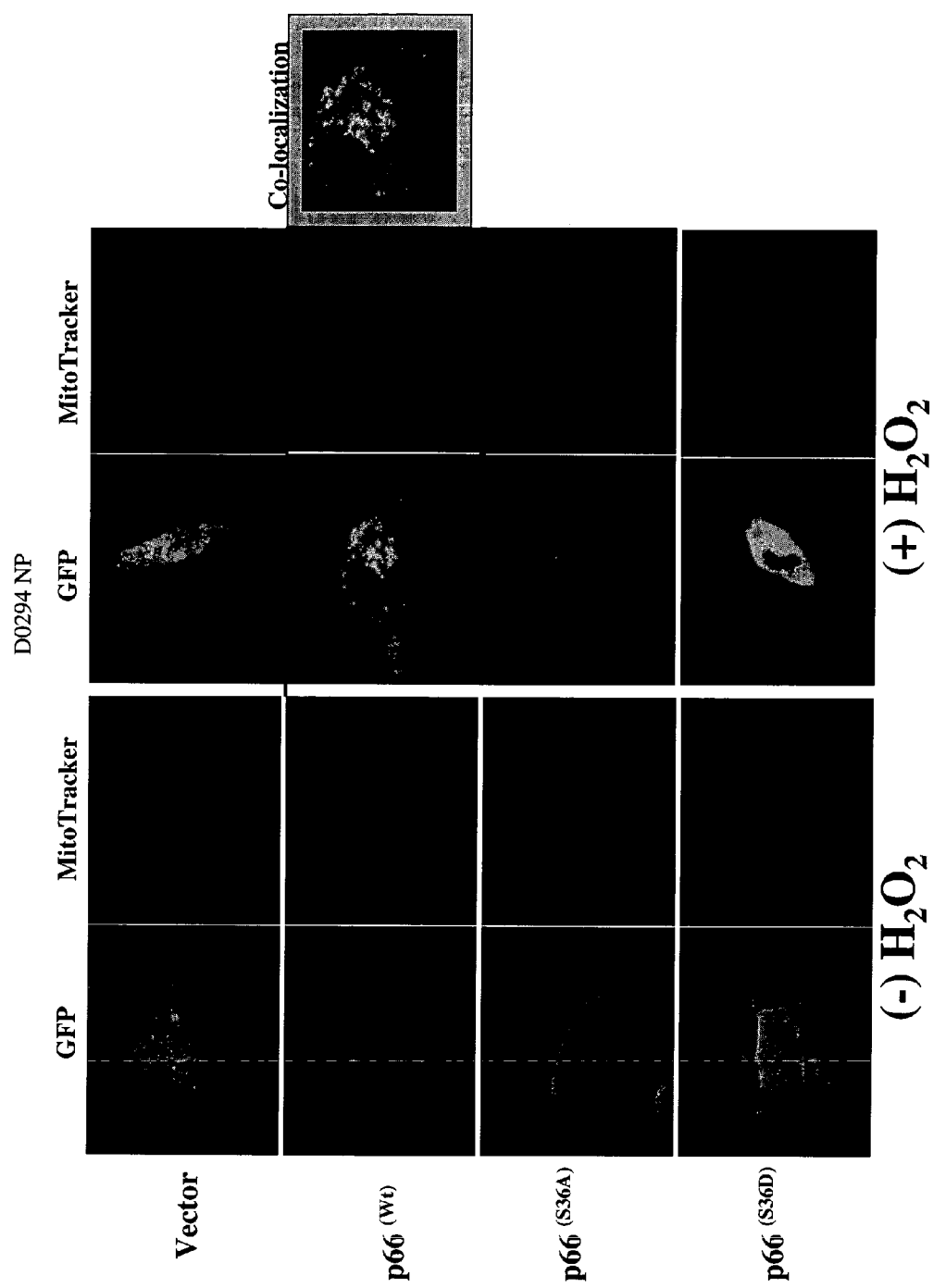
FIG. 6 is a compilation of images illustrating that wild-type $p66^{ShcA}$-GFP protein, but not the mutant protein, is present in mitochondria of cells challenged with $H_2O_2$.

A compilation of images is shown in FIG. 6. HEK293 cells expressing pEGFP are shown in panels a and e, cells expressing p66$^{ShcA}$ wild-type are shown in panels b and f, cells expressing p66$^{ShcA}$ mutant S36A are shown in panels c and g and cells expressing p66$^{ShcA}$ mutant S36D are shown in panels d and h; the cells were grown in the absence (−) and presence (+) of $H_2O_2$. Live cells expressing the GFP-chimeric proteins were counter stained with MitoTracker Red (panels a'–h') to detect mitochondria. Attention is directed to the differential sequestration of wild-type p66$^{ShcA}$ protein into MitoTracker positive mitochondria when cells are treated with $H_2O_2$ (compare panels b and f). Co-localization of the two signals (p66$^{ShcA}$-GFP and MitoTracker Red) is evident in panel i, to the right of FIG. 6 and framed in gray.

This analysis reveals a redistribution and accumulation of p66$^{ShcA}$ wild-type protein from the cytoplasm to mitochondria upon exposure to $H_2O_2$ (FIG. 6, panel f) relative to those that were not challenged by peroxide (FIG. 6, panel b). When the p66$^{ShcA}$-GFP signal is over-laid with that of MitoTracker-Red, a clear coincidence of both signals is visible (see FIG. 6, panel i, image framed in gray). The two point mutants (S36A and S36D) fail to accumulate in mitochondria and are found dispersed throughout the cytoplasm in a diffused pattern even when challenged with peroxide (FIG. 6, panels g and h). Substitution of a negatively charged amino acid (S36D) at the serine 36 position is not sufficient to induce mitochondrial accumulation of the protein and similar observations were made with the alanine substitution mutant. This observation constitutes the first direct molecular evidence implicating serine 36 phosphorylation in the regulation of p66$^{ShcA}$ targeting to mitochondria on peroxide The precise molecular mechanism (possibly via a chaperone) involved in this event is under study. Pelicci and colleagues (Migliaccio et al., (1999) *Nature* 402:309–13) have shown that the S36A mutant of p66$^{ShcA}$ is incapable of oxidative stress response mediated cell death. Additionally, it was observed that the level of intracellular hydrogen peroxide is significantly increased (>10 fold) in wild-type p66$^{ShcA}$ MEFs relative to p66$^{ShcA-/-}$ MEFs when subjected to a mild stress such as serum starvation (Nemoto & Finkel, (2002) *Science* 295:2450–52). In light of these observations and those reported in the present disclosure the effect of peroxide treatment on the various p66$^{ShcA}$ stable cells relative to pEGFP control cells with regard to their mitochondrial membrane potential and function was evaluated.

Example 15

Determination of the Integrity of Mitochondria

One of the mechanisms for ammonia toxicity in primary cultures of rat astrocytes is impared cellular bioenergetics due to changes in MPT, where mitochondrial membrane potential was measured by selective cell-permeant fluorescent dyes such as tetramethylrhodamine derivatives (TMRE, TMRM and TMR-Cl) and Rhodamine 123 (Bai et al., (2001) *J. Neurosci. Res.* 66:981–91). Therefore, in one aspect of the present invention a similar approach was employed to determine the integrity of mitochondria with reference to $\Delta_{\psi_m}$ in cells that constitutively expressed pEGFP, p66$^{ShcA}$ and the two mutant ShcA proteins ie., S36A and S36D.

Figure 7:
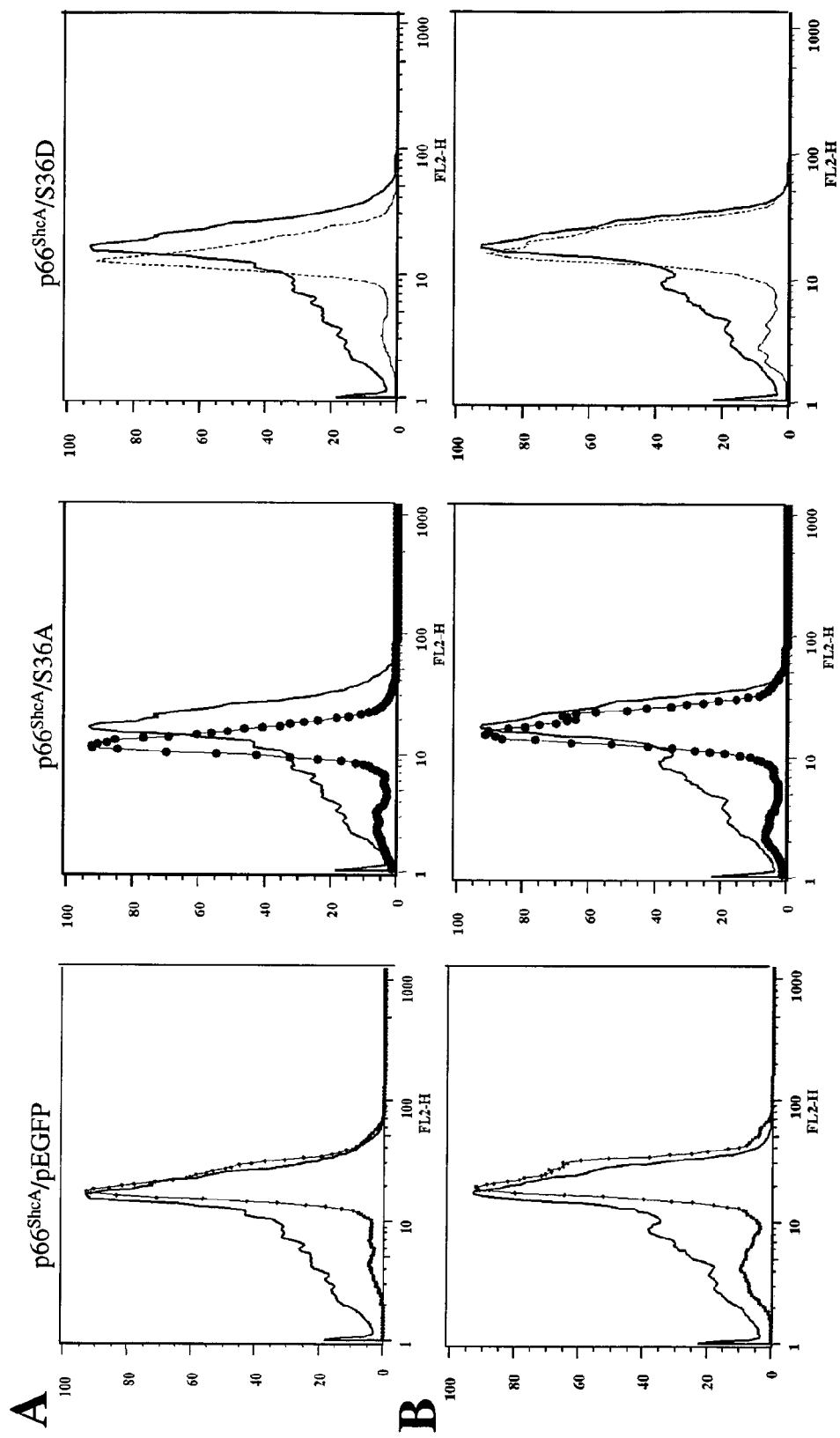
FIGS. 7A and 7B are a series of plots depicting the depolarization of the mitochondrial membrane ($\Delta\psi_m$) from cells that express $p66^{ShcA}$ relative to pEGFP and ShcA mutants that were grown in the absence of $H_2O_2$ (FIG. 7A) or the presence of $H_9O_2$ (FIG. 7B).

Cells were cultured in the absence and presence of $H_2O_2$ for 4 hours and labeled with TMR-Cl and analyzed by fluorescence activated cell sorting (FACS). FIG. 7 depicts results representative of one such experiment where the $\Delta_{\psi_m}$ plot of wild-type p66$^{ShcA}$ is superimposed with that of pEGFP or S36A or S36D mutant. HEK293 cells stably expressing pEGFP, p66$^{ShcA}$ or its point mutants (S36A and S36D) were grown in the absence (FIG. 7, Panel A) or presence (FIG. 7, Panel B) of $H_2O_2$ (4 hours). Cells were loaded with TMR-Cl and their mitochondrial membrane potential ($\Delta_{\psi_m}$) was analyzed by flow cytometry. Data is plotted as cell count vs. TMR-Cl fluorescence (as measured by FL2-Height).

Cells expressing p66$^{ShcA}$ wild-type (–) show a distinct spectral shift to the left indicating mitochondrial depolarization relative to pEGFP (♦), S36A mutant (●) and S36D mutant (---), even in the absence (FIG. 7, panel A) of $H_2O_2$ treatment. Only the p66$^{ShcA}$ wild-type cells exhibit further depolarization when subjected to peroxide challenge (FIG. 7, panel B), while the others show only a minor change in $\Delta_{\psi_m}$. FIG. 7, panel A shows the relative $\Delta_{\psi_m}$ in cells that did not receive any $H_2O_2$ while FIG. 7, panel B shows the $\Delta_{\psi_m}$ in cells at the end of 4 hr of $H_2O_2$ treatment. These figures show that constitutive expression of wild-type p66$^{ShcA}$ in cells causes a leftward shift in the spectral curve (compare p66$^{ShcA}$ with pEGFP in FIG. 7, Panel A) indicating that fewer cells retained TMR-Cl in their mitochondria (i.e., depolarized) relative to vector control cells. Evidently, upon $H_2O_2$ treatment (FIG. 7, Panel B), pEGFP cells show only a modest shift in $\Delta_\psi$ relative to wild-type p66$^{ShcA}$. Attention is directed to the distinct appearance of a significant depolarized peak around $\log_{10}$ on FL2-H in case of the wild-type p66$^{ShcA}$ cells treated with $H_2O_2$. The manifestation of depolarized mitochondria is not apparent in cells expressing the two p66$^{ShcA}$ point mutants, S36A and S36D relative to the cells expressing wild-type protein. The change in $\Delta_{\psi_m}$ in the two mutants is comparable to that of the pEGFP control cells before and after $H_2O_2$ treatment. On the contrary, a significant increase in the basal level of mitochondrial depolarization is peculiar only to the cells with ectopic wild-type p66$^{ShcA}$ expression, and the mitochondrial depolarization is further exaggerated upon peroxide treatment. These findings implicate p66$^{ShcA}$ in mitochondrial functioning specifically related to the alteration of inner mitochondrial membrane potential and maintenance of cellular redox balance associated with this organelle.

Example 16

Generation of Polyclonal Antibodies Specific for the Protein Complexes

As described in the present disclosure, p66$^{ShcA}$ interacts with prohibitin to form a complex. A complex of the two proteins can be prepared, for example, by mixing purified preparations of each of the two proteins. The protein complex can be stabilized by cross-linking the proteins in the complex, by employing methods known to those of ordinary skill in the art. The protein complex can be used to immunize rabbits and mice using a procedure similar to that described by Harlow et al. (Harlow et al., (1988) *Antibodies: A Laboratory Manual*, Cold Spring Harbor Laboratory, Cold Spring Harbor, N.Y.). This procedure has been shown to generate antibodies against various other proteins (see, e.g., Kraemer et al., (1993) *J. Lipid Res.* 34:663–672).

Briefly, purified protein complex is used as an immunogen in rabbits. Rabbits are immunized with 100 μg of the protein in complete Freund's adjuvant and boosted twice, in three-week intervals, first with 100 μg of immunogen in incomplete Freund's adjuvant, and followed by 100 μg of immunogen in PBS. Antibody-containing serum is collected two weeks thereafter. The antisera is preadsorbed with p66$^{ShcA}$ and prohibitin, such that the remaining antisera comprises antibodies which bind conformational epitopes, for example, complex-specific epitopes, present on the p66$^{shcA}$/prohibitin complex but not on the monomers.

Polyclonal antibodies against each of the complexes set forth in Table 1 are prepared in a similar manner by mixing the specified proteins together, immunizing an animal and isolating antibodies specific for the protein complex, but not for the individual proteins.

Example 17

Generation of Monoclonal Antibodies Specific for Protein Complexes

Monoclonal antibodies can be generated according to the following protocol. Mice are immunized with immunogen comprising P66$^{shcA}$/prohibitin complexes. The complexes can be prepared as described in Example 16, and may also be stabilized by cross-linking. The immunogen is mixed with an adjuvant. Each mouse receives four injections of 10 to 100 μg of immunogen, and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single-cell suspension is prepared (Harlow et al., (1988) *Antibodies: A Laboratory Manual*, Cold Spring Harbor Laboratory, Cold Spring Harbor, N.Y.). Cell fusions are performed essentially as described by Kohler & Milstein (Kohler & Milstein, (1975) *Nature* 256:495–497). Briefly, P3.65.3 myeloma cells (American Type Culture Collection, Rockville, Md.) or NS-1 myeloma cells are fused with immune spleen cells using polyethylene glycol as described by Harlow et al. (Harlow et al., (1988) *Antibodies: A Laboratory Manual*, Cold Spring Harbor Laboratory, Cold Spring Harbor, N.Y.). Cells are plated at a density of 2×10$^5$ cells/well in 96-well tissue culture plates. Individual wells are examined for growth, and the supernatants of wells with growth are tested for the presence of p66$^{shcA}$/prohibitin complex-specific antibodies by ELISA or RIA using p66$^{shcA}$/prohibitin complex as target protein. Cells in positive wells are expanded and subcloned to establish and confirm monoclonality.

Clones with the desired specificities are expanded and grown as ascites in mice or in a hollow fiber system to produce sufficient quantities of antibodies for characterization and assay development. Antibodies are tested for binding to p66$^{shcA}$ alone or to prohibitin alone, to determine which are specific for the p66$^{shcA}$/prohibitin complex as opposed to those that bind to the individual proteins.

Monoclonal antibodies against each of the complexes set forth in Table 1 can be prepared in a similar manner by mixing the specified proteins together, immunizing an animal, fusing spleen cells with myeloma cells and isolating clones which produce antibodies specific for the protein complex, but not for the individual proteins.

Example 18

In vitro Identification of Modulators for Protein-Protein Interactions

The present invention is useful in screening for agents that modulate (i.e., enhance or inhibit) the interaction of p66$^{shcA}$ and prohibitin. The knowledge that p6$^{shcA}$ and prohibitin form a complex is useful in designing such assays. Candidate agents are screened by mixing p66$^{shcA}$ and prohibitin (a) in the presence of a candidate agent, and (b) in the absence of the candidate agent. The amount of complex formed is measured for each sample. An agent modulates the interaction of p66$^{shcA}$ and prohibitin if the amount of complex formed in the presence of the agent is greater than (promoting the interaction), or less than (inhibiting the interaction) the amount of complex formed in the absence of the agent. The amount of complex is measured by a binding assay, which shows the formation of the complex, or by using antibodies immunoreactive to the complex.

Briefly, a binding assay is performed in which immobilized p66$^{shcA}$ is used to bind labeled prohibitin. The labeled prohibitin is contacted with the immobilized p66$^{shcA}$ under aqueous conditions that permit specific binding of the two proteins to form a p66$^{shcA}$/prohibitin complex in the absence of an added test agent. Particular aqueous conditions may be selected according to conventional methods. Any reaction condition can be used as long as specific binding of p66$^{shcA}$/prohibitin occurs in the control reaction. A parallel binding assay is performed in which the test agent is added to the reaction mixture. The amount of labeled prohibitin bound to the immobilized p66$^{shcA}$ is determined for the reactions in the absence or presence of the test agent. If the amount of bound, labeled prohibitin in the presence of the test agent is different than the amount of bound labeled prohibitin in the absence of the test agent, the test agent is a modulator of the interaction of p66$^{shcA}$ and prohibitin.

Candidate agents for modulating the interaction of each of the protein complexes set forth in Table 1 are screened in vitro in a similar manner.

Example 19

In Vivo Identification of Modulators for Protein-Protein Interactions

In addition to the in vivo method described in Example 18, an in vivo assay can also be used to screen for agents that modulate the interaction of p66$^{shcA}$ and prohibitin. Briefly, a yeast two-hybrid system is used in which the yeast cells express (1) a first fusion protein comprising p66$^{shcA}$ or a fragment thereof and a first transcriptional regulatory protein sequence, e.g., GAL4 activation domain, (2) a second fusion protein comprising prohibitin or a fragment thereof and a second transcriptional regulatory protein sequence, for example, GAL4 DNA-binding domain, and (3) a reporter gene, for example, β-galactosidase, which is transcribed when an intermolecular complex comprising the first fusion protein and the second fusion protein is formed. Parallel reactions are performed in the absence of a test agent as the control and in the presence of the test agent. A functional p66$^{shcA}$/prohibitin complex is detected by detecting the amount of reporter gene expressed. If the amount of reporter gene expression in the presence of the test agent is different than the amount of reporter gene expression in the absence of the test agent, the test agent is a modulator of the interaction of p66$^{shcA}$ and prohibitin.

Candidate agents for modulating the interaction of each of the protein complexes set forth in Table 1 are screened in vivo in a similar manner.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, and are within the spirit of the invention and the scope of the appended claims.

What is claimed is:

1. An isolated protein complex comprising a $p66^{ShcA}$ protein and a prohibitin protein.

2. The isolated protein complex of claim 1, wherein the protein complex comprises a $p66^{ShcA}$ sequence encoded by a polynucleotide comprising SEQ ID NO:1 and a prohibitin sequence encoded by a polynucleotide comprising SEQ ID NO:2.

3. An isolated protein complex comprising a mutated $p66^{ShcA}$ protein comprising a mutation selected from the group consisting of S36A (encoded by a polynucleotide comprising SEQ ID NO:7) and S36D (encoded by a polynucleotide comprising SEQ ID NO:8) and a prohibition protein encoded by a polynucleotide comprising SEQ ID NO: 2.

4. An isolated protein complex comprising a $p66^{ShcA}$ fragment encoded by a fragment of SEQ ID NO:1, and a prohibitin protein encoded by a polynucleotide comprising SEQ ID NO:2.

5. An isolated protein complex comprising a $p66^{ShcA}$ protein encoded by a polynucleotide comprising SEQ ID NO: 1 and a prohibitin fragment encoded by a polynucleotide comprising a fragment of SEQ ID NO: 2.

6. An isolated protein complex comprising a fragment of a p66ShcA protein encoded by a fragment of SEQ ID NO:1 and a fragment of a prohibitin protein encoded by a fragment of SEQ ID NO:2.

7. An isolated protein complex comprising a mutated $p66^{ShcA}$ protein wherein the mutation is selected from the group consisting of S36A (encoded by a polynucleotide comprising SEQ ID NO:7) and S36D (encoded by a polynucleotide comprising SEQ ID NO:8) and a prohibitin fragment encoded by a polynucleotide comprising a fragment of SEQ ID NO:2.

8. A method of identifying a compound capable of modulating the formation of a $p66^{ShcA}$-prohibitin protein complex comprising the steps of:
   (a) combining a $p66^{ShcA}$ protein and a prohibitin protein in the presence of a test compound;
   (b) combining a $p66^{ShcA}$ protein and a prohibitin protein in the absence of the test compound;
   (c) measuring the amount of $p66^{ShcA}$ protein and a prohibitin protein complex formation in the presence and absence of the test compound and;
   (d) comparing the amount of the $p66^{ShcA}$ protein and prohibitin protein complex formation in the presence and absence of the test compound;
   wherein if the amount of the complex formation in the presence of the test compound is less than the amount of the complex formation in the absence of the test compound, then the test compound reduces the formation of the protein complex.

9. The method of claim 8, wherein the $p66^{ShcA}$ is encoded by a polynucleotide comprising the sequence of SEQ ID NO:1.

10. The method of claim 8, wherein the prohibitin is encoded by a polynucleotide comprising the sequence of SEQ ID NO:2.

11. A method of identifying a compound capable of modulating the formation of a mutated $p66^{ShcA}$-prohibitin protein complex comprising the steps of:
   (a) combining a mutated $p66^{ShcA}$ protein and a prohibitin protein in the presence of a test compound;
   (b) combining a mutated $p66^{ShcA}$ protein and a prohibitin protein in the absence of a test compound;
   (c) measuring the amount of mutated $p66^{ShcA}$ protein and a prohibitin protein complex formation in the presence and absence of the test compound and;
   (d) comparing the amount of the mutated $p66^{ShcA}$ protein and prohibitin protein complex formation in the presence and absence of the test compound;
   wherein if the amount of complex formation in the presence of the test compound is less than the amount of complex formation in the absence of the test compound, then the test compound reduces the formation of the protein complex.

12. The method of claim 11, wherein the prohibitin protein is encoded by a polynucleotide comprising the sequence of SEQ ID NO:2.

13. The method of claim 11, wherein the mutated p66ShcA protein is encoded by a polynucleotide selected from the group consisting of SEQ ID NO:7 and SEQ ID NO:8.

* * * * *

SEQUENCE LISTING

```
<160> NUMBER OF SEQ ID NOS: 8

<210> SEQ ID NO 1
<211> LENGTH: 1752
<212> TYPE: DNA
<213> ORGANISM: human

<400> SEQUENCE: 1
atggatctcc tgcccccaa gcccaagtac aatccactcc ggaatgagtc tctgtcatcg      60
ctggaggaag gggcttctgg gtccaccccc ccggaggagc tgccttcccc atcagcttca     120
tccctggggc ccatcctgcc tcctctgcct ggggacgata gtcccactac cctgtgctcc     180
ttcttccccc ggatgagcaa cctgaggctg gccaacccgg ctggggggcg cccagggtct     240 aaggggagc caggaagggc agctgatgat ggggagggga tcgatgggc agccatgcca       300 gagtcaggcc ccctaccct cctccaggac atgaacaagc tgagtggagg cggcgggcgc      360
aggactcggg tggaaggggg ccagcttggg ggcgaggagt ggacccgcca cgggagcttt     420
gtcaataagc ccacgcgggg ctggctgcat cccaacgaca aagtcatggg acccggggtt     480
```

-continued

```
tcctacttgg ttcggtacat gggttgtgtg gaggtcctcc agtcaatgcg tgccctggac    540
ttcaacaccc ggactcaggt caccagggag gccatcagtc tggtgtgtga ggctgtgccg    600
ggtgctaagg gggcgacaag gaggagaaag ccctgtagcc gcccgctcag ctctatcctg    660
gggaggagta acctgaaatt tgctggaatg ccaatcactc tcaccgtctc caccagcagc    720
ctcaacctca tggccgcaga ctgcaaacag atcatcgcca accaccacat gcaatctatc    780
tcatttgcat ccggcgggga tccggacaca gccgagtatg tcgcctatgt tgccaaagac    840
cctgtgaatc agagagcctg ccacattctg gagtgtcccg aagggcttgc ccaggatgtc    900
atcagcacca ttggccaggc cttcgagttg cgcttcaaac aatacctcag gaacccaccc    960
aaactggtca cccctcatga caggatggct ggctttgatg gctcagcatg ggatgaggag   1020
gaggaagagc cacctgacca tcagtactat aatgacttcc cggggaagga acccccttg    1080 gggggggtgg tagacatgag gcttcgggaa ggagccgctc caggggctgc tcgacccact   1140
gcacccaatg cccagacccc cagccacttg ggagctacat tgcctgtagg acagcctgtt   1200
gggggagatc cagaagtccg caaacagatg ccacctccac caccctgtcc aggcagagag   1260 cttttttgatc atccctccta tgtcaacgtc cagaacctag acaaggcccg gcaagcagtg   1320
ggtggtgctg ggcccccccaa tcctgctatc aatggcagtg caccccggga cctgtttgac   1380
atgaagccct tcgaagatgc tcttcgggtg cctccacctc cccagtcggt gtccatggct   1440
gagcagctcc gaggggagcc ctggttccat gggaagctga gccggcggga ggctgaggca   1500
ctgctgcagc tcaatgggga cttcttggta cgggagagca cgaccacacc tggccagtat   1560
gtgctcactg gcttgcagag tgggcagcct aagcatttgc tactggtgga ccctgagggt   1620
gtggttcgga ctaaggatca ccgctttgaa agtgtcagtc accttatcag ctaccacatg   1680
gacaatcact tgcccatcat ctctgcgggc agcgaactgt gtctacagca acctgtggag   1740
cggaaactgt ga                                                       1752
```

<210> SEQ ID NO 2
<211> LENGTH: 819
<212> TYPE: DNA
<213> ORGANISM: human

<400> SEQUENCE: 2

```
atggctgcca aagtgtttga gtccattggc aagtttggcc tggccttagc tgttgcagga     60
ggcgtggtga actctgcctt atataatgtg gatgctgggc acagagctgt catctttgac    120
cgattccgtg gagtgcagga cattgtggta ggggaaggga ctcattttct catcccgtgg    180
gtacagaaac caattatctt tgactgccgt tctcgaccac gtaatgtgcc agtcatcact    240
ggtagcaaag atttacagaa tgtcaacatc acactgcgca tcctcttccg gcctgtcgcc    300
agccagcttc ctcgcatctt caccagcatc ggagaggact atgatgagcg tgtgctgccg    360
tccatcacaa ctgagatcct caagtcagtg gtggctcgct tgatgctgg agaactaatc    420 acccagagag agctggtctc caggcaggtg agcgacgacc ttacagagcg agccgccacc    480
tttgggctca tcctggatga cgtgtccttg acacatctga ccttcgggaa ggagttcaca    540
gaagcggtgg aagccaaaca ggtggctcag caggaagcag agagggccag atttgtggtg    600
gaaaaggctg agcaacagaa aaaggcggcc atcatctctg ctgagggcga ctccaaggca    660
gctgagctga ttgccaactc actggccact gcagggggatg gcctgatcga gctgcgcaag    720
ctggaagctg cagaggacat cgcgtaccag ctctcacgct tcggaacat cacctacctg    780 ccagcggggc agtccgtgct cctccagctg ccccagtga                           819
```

<210> SEQ ID NO 3
<211> LENGTH: 34
<212> TYPE: DNA
<213> ORGANISM: human

<400> SEQUENCE: 3
catatggagc cacctgacca tcagtactat aatg                                    34

<210> SEQ ID NO 4
<211> LENGTH: 30
<212> TYPE: DNA
<213> ORGANISM: human

<400> SEQUENCE: 4
gaattctcag ggctcccctc ggagctgctc                                         30

<210> SEQ ID NO 5
<211> LENGTH: 27
<212> TYPE: DNA
<213> ORGANISM: human

<400> SEQUENCE: 5
catatggatc tcctgccccc caagccc                                            27

<210> SEQ ID NO 6
<211> LENGTH: 30
<212> TYPE: DNA
<213> ORGANISM: human

<400> SEQUENCE: 6
gaattctcag tcctggagga ggggtagggg                                         30

<210> SEQ ID NO 7
<211> LENGTH: 1755
<212> TYPE: DNA
<213> ORGANISM: human

<400> SEQUENCE: 7
catatggatc tcctgccccc caagcccaag tacaatccac tccggaatga gtctctgtca        60
tcgctggagg aaggggcttc tgggtccacc ccccggagg agctgcctgc cccatcagct        120
tcatccctgg ggcccatcct gcctcctctg cctggggacg atagtcccac taccctgtgc        180
tccttcttcc cccggatgag caacctgagg ctggccaacc cggctggggg gcgcccaggg        240
tctaagggg agccaggaag ggcagctgat gatggggagg ggatcgatgg ggcagccatg        300
ccagagtcag gccccctacc cctcctccag gacatgaaca agctgagtgg aggcggcggg        360
cgcaggactc gggtggaagg gggccagctt gggggcgagg agtggacccg ccacgggagc        420
tttgtcaata gcccacgcg gggctggctg catcccaacg acaaagtcat gggacccggg        480
gtttcctact tggttcggta catgggttgt gtggaggtcc tccagtcaat gcgtgccctg        540
gacttcaaca cccggactca ggtcaccagg gaggccatca gtctggtgtg tgaggctgtg        600
ccgggtgcta aggggcgac aaggaggaga aagccctgta gccgcccgct cagctctatc        660
ctggggagga gtaacctgaa atttgctgga atgccaatca ctctcaccgt ctccaccagc        720
agcctcaacc tcatggccgc agactgcaaa cagatcatcg ccaaccacca catgcaatct        780
atctcatttg catccggcgg ggatccggac acagccgagt atgtcgccta tgttgccaaa        840
gaccctgtga atcagagagc ctgccacatt ctggagtgtc ccgaagggct tgcccaggat        900

| | | | |
|---|---|---|---|
| gtcatcagca | ccattggcca | ggccttcgag ttgcgcttca | aacaatacct caggaaccca | 960 |
| cccaaactgg | tcacccctca | tgacaggatg gctggctttg | atggctcagc atgggatgag | 1020 |
| gaggaggaag | agccacctga | ccatcagtac tataatgact | cccggggaa ggaaccccccc | 1080 |
| ttggggggg | tggtagacat | gaggcttcgg gaaggagccg | ctccagggc tgctcgaccc | 1140 |
| actgcaccca | tgcccagac | ccccagccac ttgggagcta | cattgcctgt aggacagcct | 1200 |
| gttggggag | atccagaagt | ccgcaaacag atgccacctc | caccaccctg tccaggcaga | 1260 |
| gagcttttg | atgatccctc | ctatgtcaac gtccagaacc | tagacaaggc ccggcaagca | 1320 |
| gtgggtggtg | ctgggccccc | caatcctgct atcaatggca | gtgcacccg ggacctgttt | 1380 |
| gacatgaagc | ccttcgaaga | tgctcttcgg gtgcctccac | ctccccagtc ggtgtccatg | 1440 |
| gctgagcagc | tccgaggga | gccctggttc catgggaagc | tgagccggcg ggaggctgag | 1500 |
| gcactgctgc | agctcaatgg | ggacttcctg gtacgggaga | gcacgaccac acctggccag | 1560 |
| tatgtgctca | ctggcttgca | gagtgggcag cctaagcatt | tgctactggt ggaccctgag | 1620 |
| ggtgtggttc | ggactaagga | tcaccgcttt gaaagtgtca | gtcaccttat cagctaccac | 1680 |
| atggacaatc | acttgcccat | catctctgcg ggcagcgaac | tgtgtctaca gcaacctgtg | 1740 |
| gagcggaaac | tgtga | | | 1755 |

```
<210> SEQ ID NO 8
<211> LENGTH: 1752
<212> TYPE: DNA
<213> ORGANISM: human

<400> SEQUENCE: 8
```

| | | | |
|---|---|---|---|
| atggatctcc | tgccccccaa | gcccaagtac aatccactcc | ggaatgagtc tctgtcatcg | 60 |
| ctggaggaag | gggcttctgg | gtccaccccc ccggaggagc | tgcctgaccc atcagcttca | 120 |
| tccctggggc | catcctgcc | tcctctgcct ggggacgata | gtcccactac cctgtgctcc | 180 |
| ttcttcccc | ggatgagcaa | cctgaggctg gccaacccgg | ctgggggcg cccagggtct | 240 |
| aaggggagc | caggaagggc | agctgatgat gggagggga | tcgatgggc agccatgcca | 300 |
| gagtcaggcc | ccctacccct | cctccaggac atgaacaagc | tgagtggagg cggcgggcgc | 360 |
| aggactcggg | tggaagggg | ccagcttggg ggcgaggagt | ggacccgcca cgggagcttt | 420 |
| gtcaataagc | ccacgcgggg | ctggctgcat cccaacgaca | aagtcatggg acccggggtt | 480 |
| tcctacttgg | ttcggtacat | gggttgtgtg gaggtcctcc | agtcaatgcg tgccctggac | 540 |
| ttcaacaccc | ggactcaggt | caccagggag gccatcagtc | tggtgtgtga ggctgtgccg | 600 |
| ggtgctaagg | gggcgacaag | gaggagaaag ccctgtagcc | gccgctcag ctctatcctg | 660 |
| gggaggagta | acctgaaatt | tgctggaatg ccaatcactc | tcaccgtctc caccagcagc | 720 |
| ctcaacctca | tggccgcaga | ctgcaaacag atcatcgcca | accaccacat gcaatctatc | 780 |
| tcatttgcat | ccggcgggga | tccggacaca gccgagtatg | tcgcctatgt tgccaaagac | 840 |
| cctgtgaatc | agagagcctg | ccacattctg gagtgtcccg | aagggcttgc ccaggatgtc | 900 |
| atcagcacca | ttggccaggc | cttcgagttg cgcttcaaac | aatacctcag gaacccaccc | 960 |
| aaactggtca | cccctcatga | caggatggct ggctttgatg | gctcagcatg ggatgaggag | 1020 |
| gaggaagagc | cacctgacca | tcagtactat aatgacttcc | ggggaagga accccccttg | 1080 |
| ggggggtgg | tagacatgag | gcttcgggaa ggagccgctc | agggctgc tcgacccact | 1140 |
| gcacccaatg | cccagacccc | cagccacttg ggagctacat | gcctgtaggg acagcctgtt | 1200 |
| ggggagatc | cagaagtccg | caaacagatg ccacctccac | caccctgtcc aggcagagag | 1260 |

```
cttttgatg atccctccta tgtcaacgtc cagaacctag acaaggcccg gcaagcagtg    1320
ggtggtgctg ggcccccaa tcctgctatc aatggcagtg caccccggga cctgtttgac    1380
atgaagccct tcgaagatgc tcttcgggtg cctccacctc cccagtcggt gtccatggct    1440
gagcagctcc gagggagcc ctggttccat gggaagctga gccggcggga ggctgaggca    1500
ctgctgcagc tcaatgggga cttcctggta cgggagagca cgaccacacc tggccagtat    1560
gtgctcactg gcttgcagag tgggcagcct aagcatttgc tactggtgga ccctgagggt    1620
gtggttcgga ctaaggatca ccgctttgaa agtgtcagtc accttatcag ctaccacatg    1680
gacaatcact tgcccatcat ctctgcgggc agcgaactgt gtctacagca acctgtggag    1740
cggaaactgt ga                                                        1752
```